(12) United States Patent
Kim

(10) Patent No.: US 7,226,418 B2
(45) Date of Patent: Jun. 5, 2007

(54) AUTOMATIC BLOOD PRESSURE MEASURING INSTRUMENT AND METHOD THEREOF

(76) Inventor: You-In Kim, 204-702, Buyoung 2-Cha APT, Yongam-dong, Sangdang-gu, Cheongju, Chungcheongbuk-do (KR)

( * ) Notice: Subject to any disclaimer, the term of this patent is extended or adjusted under 35 U.S.C. 154(b) by 0 days.

(21) Appl. No.: 10/525,771

(22) PCT Filed: Aug. 30, 2003

(86) PCT No.: PCT/KR03/01772

§ 371 (c)(1),
(2), (4) Date: Feb. 28, 2005

(87) PCT Pub. No.: WO2004/019754

PCT Pub. Date: Mar. 11, 2004

(65) Prior Publication Data

US 2005/0251059 A1    Nov. 10, 2005

(30) Foreign Application Priority Data

Aug. 31, 2002  (KR) ............... 10-2002-0052213

(51) Int. Cl.
*A61B 5/02* (2006.01)
*A61B 5/04* (2006.01)
(52) U.S. Cl. .............. 600/485; 600/500; 600/509
(58) Field of Classification Search ............ None
See application file for complete search history.

(56) References Cited

U.S. PATENT DOCUMENTS

| | | | | |
|---|---|---|---|---|
| 3,903,873 A | * | 9/1975 | Royal et al. ............ | 600/502 |
| 4,442,845 A | * | 4/1984 | Stephens ............... | 600/500 |
| 4,742,831 A | * | 5/1988 | Silvian ................. | 600/523 |
| 4,754,406 A | * | 6/1988 | Miyawaki et al. ...... | 600/493 |
| 5,027,824 A | * | 7/1991 | Dougherty et al. ..... | 600/515 |
| 5,735,799 A | * | 4/1998 | Baba et al. ............ | 600/500 |
| 5,873,834 A | * | 2/1999 | Yanagi et al. ......... | 600/485 |
| 2001/0012916 A1 | | 8/2001 | Deuter | |
| 2002/0095092 A1 | * | 7/2002 | Kondo et al. .......... | 600/503 |
| 2003/0125631 A1 | * | 7/2003 | Amano ................. | 600/500 |

FOREIGN PATENT DOCUMENTS

FR    2 514 633    4/1983

* cited by examiner

*Primary Examiner*—Charles A. Marmor, II
*Assistant Examiner*—Patricia Mallari
(74) *Attorney, Agent, or Firm*—Stein, McEwen & Bui, LLP

(57) ABSTRACT

An automatic blood pressure measuring instrument for measuring and displaying a blood pressure of a subject in a non-invasive manner includes a pressure sensor for obtaining a pulse wave signal from a wrist of the subject, a pulse wave signal processing section for amplifying, filtering, and removing noise from the pulse wave applied from the pressure sensor, electrocardiogram electrodes for obtaining an electrocardiogram signal of the subject, an electrocardiogram signal processing section for amplifying, filtering, and removing noise from the electrocardiogram signal, an A/D converting section for converting the pulse wave signal the electrocardiogram signal into digital signals, a controlling section for comparing and analyzing the digital pulse wave signal and the digital electrocardiogram signal to determine the blood pressure of the subject, and a display for displaying the blood pressure of the subject determined by the controlling section.

17 Claims, 18 Drawing Sheets

AUTOMATIC BLOOD PRESSURE MEASURING INSTRUMENT AND METHOD THEREOF

CROSS-REFERENCE TO RELATED APPLICATIONS

This application is the U.S. National Stage of International Application No. PCT/KR2003/001772 filed on Aug. 30, 2003, and claims the benefit of Korean Application No. 2002-52213 filed on Aug. 31, 2002, in the Korean Intellectual Property Office.

BACKGROUND OF THE INVENTION

1. Field of the Invention

An aspect of invention relates to a blood pressure measuring instrument, and more particularly, to an automatic blood pressure measuring instrument and method designed to obtain a pulse wave signal and an electrocardiogram (ECG) signal from a pressure sensor and ECG electrodes, to analyze a correlation between both signals, to determine a maximum blood pressure and a minimum blood pressure based on the analyzed data, and to output the determined result to a display.

2. Description of the Related Art

As the number of the home health aged has been increased due to the general aging of society, a gradually increasing attention has been drawn to welfare and care for the aged. Thus, the approach of an elderly health care has begun to occur in a new scheme at various angles, and a concentrated attention has been paid to a blood pressure measurement functioning as the basis of health check-up.

Measurement of a blood pressure, as one of current generalized clinical tests, is carried out while a doctor performs an examination or a particular surgical operation. Further, values of blood pressure, which are measured in respective ventricle and atrium of the heart or in a peripheral vascular system, function as a basis of health check-up helpful to enable the doctor to understand an integrated function between vascular and cardiac systems.

A blood pressure refers to one generated when blood flowing a blood vessel acts on a wall of the blood vessel, and is determined by a quantity of the blood and a resistance of the blood vessel, such as elasticity, expansion, contraction and so on. Measurement of the blood pressure allows for estimation of a function of the heart or the blood vessel. To be more specific, while the heart is contracted, the blood is driven to circulate around the whole body. The pressure of the driven blood, or the maximum blood pressure, represents a contractile force of the heart. The minimum blood pressure when the heart is expanded can be considered as an index indicating how smoothly the blood circulates through the blood vessel.

The human blood vessel consists of an artery through which blood exits from the heart toward the whole body, a vein through which blood enters from the whole body toward the heart, and a capillary vessel interconnecting between the artery and the vein. In general, a pressure in the artery, i.e., an arterial blood pressure, is called a "blood pressure." This blood pressure is very different according to size and position of the blood vessel, and is sequentially lowered in the order of an aorta, an artery, an arteriole, a capillary vessel, a veinlet, a vein and a hollow. For this reason, the blood pressure is named for the name of the blood vessel, for example, as an aortic blood pressure, an arterial blood pressure, an arteriole blood pressure and so forth. The arterial blood pressure maintained by heartbeats is one of fundamental, usual clinical symptoms estimating a function between the vascular and cardiac systems, and a factor taking part in perfusion of the entire tissues, or particularly having an important influence on a cerebral blood flow and a coronary blood flow.

As existing blood pressure measuring methods, there are an invasive one and non-invasive one. The invasive method inserts a catheter directly into an artery to measure the blood pressure. However, it requires much trouble and heavy cost in measuring the blood pressure, and has various disadvantages, such as circulatory problem of the blood, infection, blood clot and so on, in the course of inserting the catheter into the artery. For these reasons, the invasive method has been used in an extremely limited range. By contrast, the non-invasive method mainly makes use of a cuff. However, the non-invasive method is not only very inaccurate, but also is responsible for a tissular trauma. Further, it is impossible to apply to infants or low blood pressure patients, and above all to perform continuous monitoring. Additionally, an electronic hemadynamometer, which has been frequently used at the present time, shows a tendency of its accuracy to be significantly lowered when the blood pressure is less than 70 mmHg.

To measure the blood pressure, there have been many attempts to make use of a pulse wave velocity. Further, there has been devised a blood pressure estimating method using the pulse wave velocity or a pulse arrival time by many persons. However, in the case of using only the pulse wave velocity or the pulse arrival time, it is impossible to ensure accomplishment of reliable blood pressure monitoring

SUMMARY OF THE INVENTION

An aspect of the invention is to provide an automatic blood pressure measuring instrument and method capable of measuring a blood pressure even though infants, low blood pressure patients, intensive care patients, etc., cannot be measured by an existing blood pressure measuring instrument, and capable of expanding an application range as a vascular automatic diagnosis device using a pulse wave signal, including a simple blood pressure measurement.

Another aspect of the invention is to provide an automatic blood pressure measuring instrument and method capable not only of continuously measuring systolic and diastolic blood pressures for a short and long time, but also of monitoring for a long time by a non-invasive method.

In accordance with an aspect of the invention, an automatic blood pressure measuring instrument for measuring and displaying a blood pressure of a subject in a non-invasive manner includes a pressure sensor for obtaining a pulse wave signal from a wrist of the subject; a pulse wave signal processing section for amplifying, filtering and noise-removing the pulse wave signal applied from the pressure sensor; electrocardiogram electrodes for detecting an electrocardiogram signal of the subject; an electrocardiogram signal processing section for amplifying, filtering and noise-removing the electrocardiogram signal detected by the electrocardiogram electrodes; an A/D converting section for converting the analog signals, which are applied from both the pulse wave signal processing section and the electrocardiogram signal processing section, into digital signals; a controlling section for comparing and analyzing the pulse wave signal and the electrocardiogram signal applied through the A/D converting section to determine the blood pressure of the subject; and a display for displaying the blood pressure of the subject determined by the controlling section.

The automatic blood pressure measuring instrument may further include a program storing section for storing an operation program of the controlling section, and a data storing section for storing the pulse wave signal and the electrocardiogram signal applied from the A/D converting section for a predetermined time and storing data determined by the controlling section.

The pulse wave signal processing section may include a first impedance matching means for matching impedances of the inputted pulse wave signal and output signal, a first low-pass filter for filtering and amplifying the signal outputted from the first impedance matching means, and a first notch filter for removing a noise of a commercial power frequency from the signal amplified at the first low-pass filter.

The first notch filter may include an operational (OP) amplifier for amplifying the signal amplified at the first low-pass filter and inputted to a non-inverting terminal thereof, a low-pass filter provided on a loop fed from an output terminal of the OP amplifier back to an inverting terminal and for removing the noise of the commercial power frequency, a first variable resistor connected in parallel with the non-inverting terminal of the OP amplifier, and a second variable resistor connected in parallel with the low-pass filter, whereby the first notch filter adjusts the cut-off frequency of the applied signals.

The electrocardiogram signal processing section may include an amplifying section for amplifying the electrocardiogram signal detected by the electrocardiogram electrodes, and a filtering section for filtering and noise-removing the signal amplified at the amplifying section.

The filtering section may include a fourth low-pass filter for removing a noise from the amplified signal applied from the amplifying section, a third impedance matching means for matching an impedance of the input signal applied from the fourth low-pass filter and an impedance of an output signal, and a second notch filter for removing the noise of the commercial power frequency from the signal applied from the third impedance matching means.

The amplifying section may include a first differential amplifier including a first gain adjusting means for adjusting a gain of the electrocardiogram signal measured from one side of a body of the subject, a second low-pass filter for removing a low band noise from the signal applied from the first gain adjusting means, and a first electrocardiogram signal amplifying means for amplifying the signal filtered at the second low-pass filter; a second differential amplifier including a second gain adjusting means for adjusting a gain of the electrocardiogram signal measured from the other side of a body of the subject, a third low-pass filter for removing a low band noise from the signal applied from the second gain adjusting means, and a second electrocardiogram signal amplifying means for amplifying the signal filtered at the third low-pass filter; and a second impedance matching means for matching an impedance with the filtering section when the amplified signals of the first and second differential amplifiers are applied.

The first and second differential amplifiers may further include an inverse current preventing means connected to input terminals to which the electrocardiogram signal is applied from the electrocardiogram electrodes.

In accordance with another aspect of the invention, an automatic blood pressure measuring method for measuring and displaying a blood pressure of a subject in a non-invasive manner includes obtaining, amplifying, and filtering an analog pulse wave signal from a wrist of the subject; obtaining, amplifying, and filtering an analog electrocardiogram signal of the subject; converting analog signals of the pulse wave signal and the electrocardiogram signal into digital signals after the amplifying and filtering operations; comparing the pulse wave signal and the electrocardiogram signal converted in the converting operation to determine the blood pressure of the subject; and displaying the blood pressure determined in the comparing operation.

The comparing operation includes comparing the pulse wave signal and the electrocardiogram signal to determine a transition time parameter, an integral parameter, an area parameter, and a maximum amplitude parameter; and determining a maximum blood pressure and a minimum blood pressure of the subject based on the transition time parameter, the integral parameter, the area parameter, and the maximum amplitude parameter.

The transition time parameter is a time interval between a maximum amplitude of a waveform of the pulse wave signal and a maximum amplitude of the electrocardiogram signal. The integral parameter is an integral value of a data value of the pulse wave signal between end points of a selected zone of the pulse wave signal. The area parameter is an integral value of a difference between a data value of the pulse wave signal between end points of a selected zone of the pulse wave signal and a value of a base line joining points where a waveform of the pulse wave signal intersects the end points of the selected zone of the pulse wave signal. The maximum amplitude parameter is a maximum amplitude of a waveform of the pulse wave signal within a selected zone of the digital pulse wave signal.

In other words, an aspect of the invention enables anyone who is not a medical expert to measure the blood pressure with ease by sensing a pulse wave signal with a pressure sensor, sensing an electrocardiogram signal with electrocardiogram electrodes, determining maximum and minimum blood pressures based on parameters determined by comparing the pulse wave signal and the electrocardiogram signal, and displaying the determined maximum and minimum blood pressures on a display.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of various embodiments, taken in conjunction with the accompanying drawings of which.

DETAILED DESCRIPTION OF THE EMBODIMENTS

Figure 1:
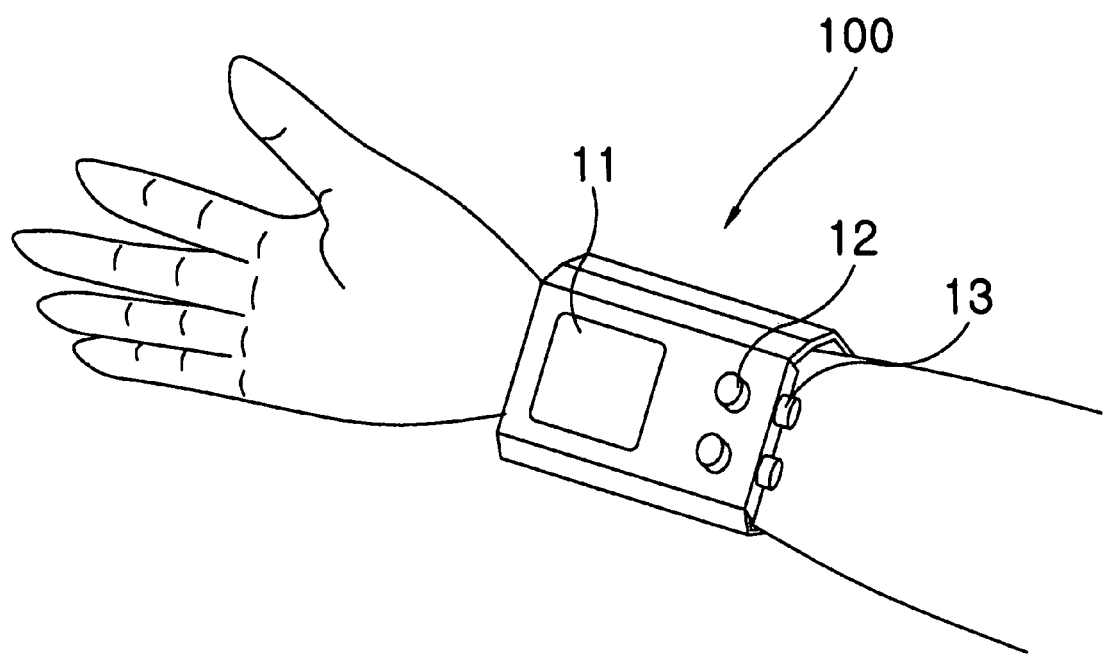
FIG. 1 is a perspective view of an automatic blood pressure measuring instrument according to an aspect of the invention attached to an arm of a subject.

Reference will now be made in detail to various embodiments of the invention, examples of which are shown in the accompanying drawings, wherein like reference numerals refer to like elements throughout. The embodiments are described below in order to explain the invention by referring to the figures.

Figure 2:
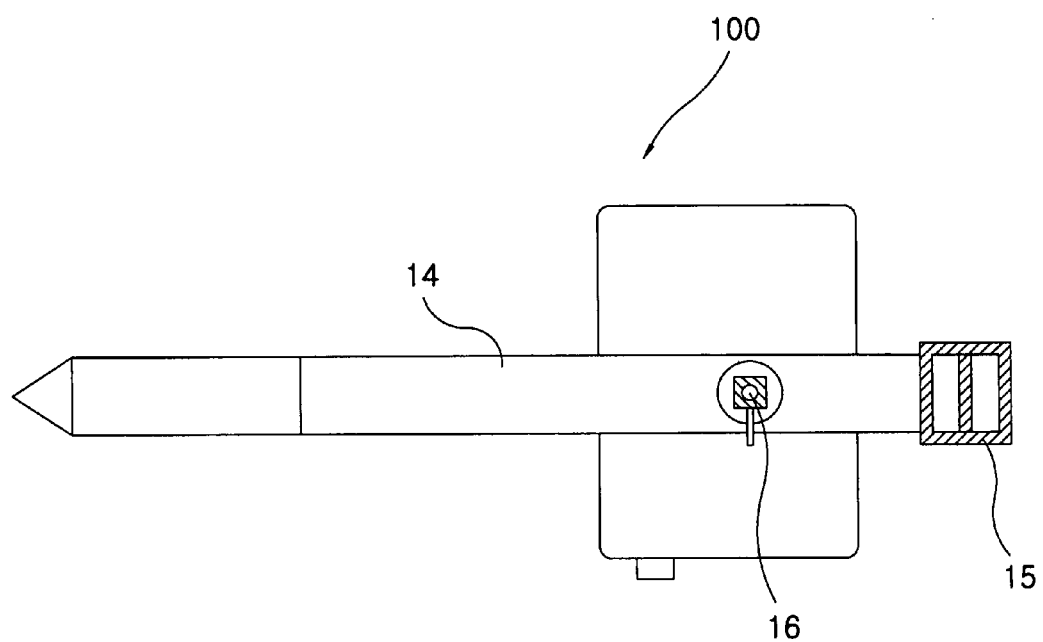
FIG. 2 is a bottom view of the automatic blood pressure measuring instrument shown in FIG. 1.
Figure 3:
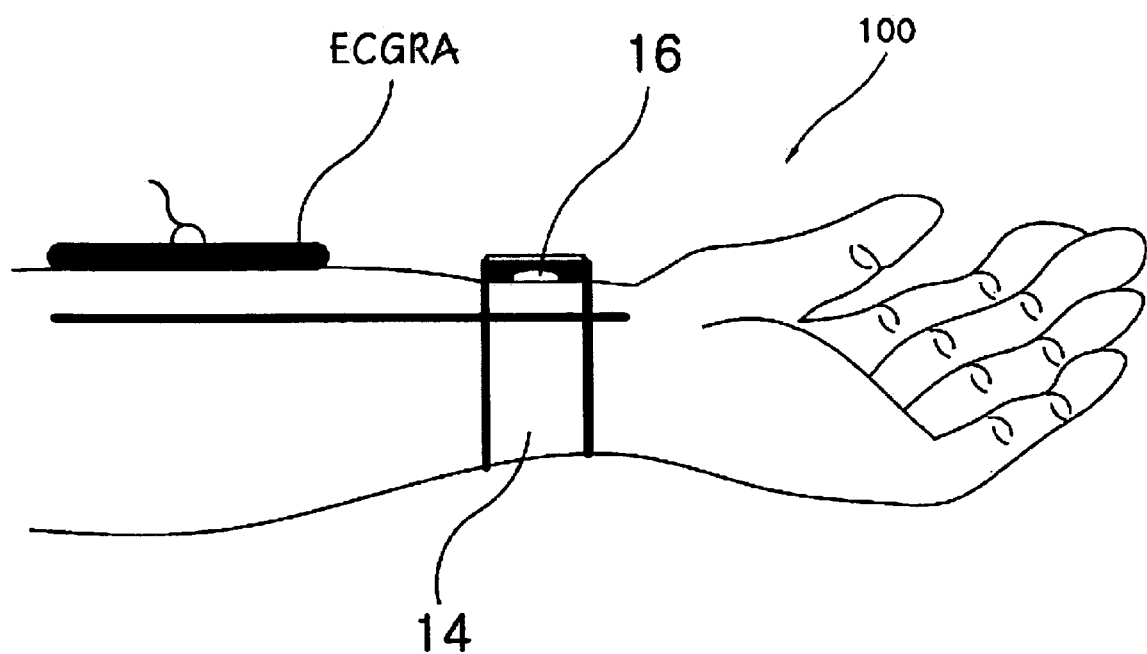
FIG. 3 is a side view of the automatic blood pressure measuring instrument shown in FIG. 1 attached to the arm of the subject.

FIG. 1 is a perspective view of an automatic blood pressure measuring instrument according to an aspect of the invention attached to an arm of a subject. FIG. 2 is a bottom view of the automatic blood pressure measuring instrument shown in FIG. 1. FIG. 3 is a side view of the automatic blood pressure measuring instrument shown in FIG. 1 attached to the arm of the subject.

A reference numeral 100 indicates an automatic blood pressure measuring instrument, 11 indicates a display, 12 indicates manipulating keys, 13 indicates electrocardiogram (ECG) electrode connection ports, 14 indicates a band, 15 indicates a buckle, 16 indicates a pressure sensor, and ECG RA indicates a second ECG electrode (also shown in FIG. 7) fixed to a right arm of a subject.

The display 11 is for displaying a measured blood pressure. The manipulating keys 12 are for inputting a manipulation signal of a user. The ECG connection ports 13 are for connecting a first ECG electrode ECG LL (shown in FIG. 7) and the second ECG electrode ECG RA to the automatic blood pressure measuring instrument 100. The first ECG electrode ECG LL is fixed to a left leg of the subject. The first ECG electrode ECG LL and the second ECG electrode ECG RA detect an ECG signal of the subject. The band 14 supports the automatic blood pressure measuring instrument 100. The buckle 15 fixedly positions the automatic blood pressure measuring instrument 100 on a wrist of the subject. The pressure sensor 16 senses a pulse wave of the subject and outputs a pulse wave signal.

In order to measure a blood pressure of the subject, first, the pressure sensor 16 is positioned over an artery of the subject. Then, the band 14 is wound around a wrist of the subject, and then the buckle 15 is fastened. Subsequently, the first ECG electrode ECG LL and the second ECG electrode ECG RA are connected to the ECG connection ports 13. Then, the first ECG electrode ECG LL is fixed to the left leg of the subject, while the second ECG electrode ECG RA is fixed to the right arm of the subject.

Therefore, the automatic blood pressure measuring instrument 100 obtains a pulse wave signal of the subject using the pressure sensor 16, and obtains an ECG signal of the subject using the first ECG electrode ECG LL and the second ECG electrode ECG RA. Thus, a controlling section 70 compares and analyzes both signals to determine the maximum and minimum blood pressures and display them on the display 11.

Figure 4:
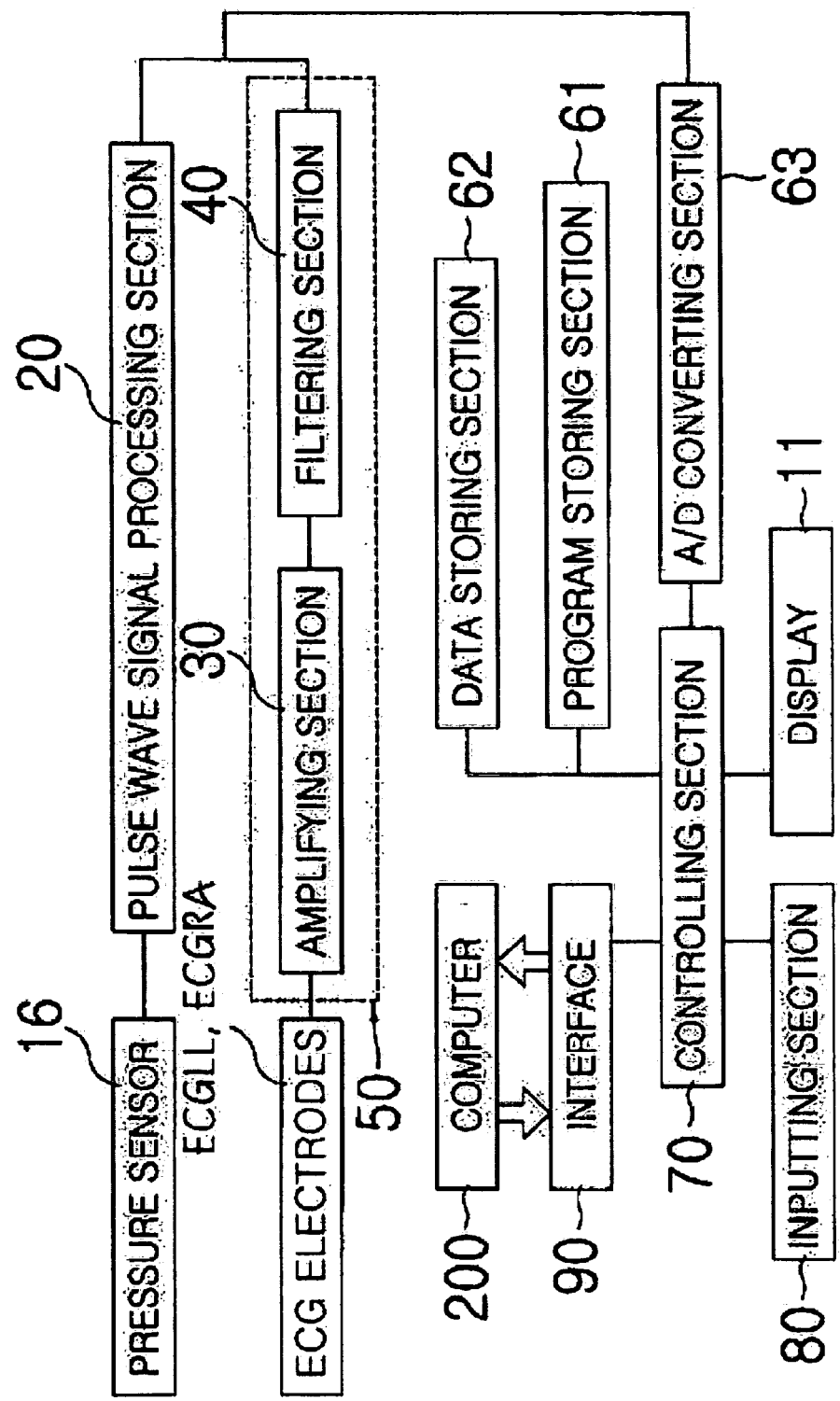
FIG. 4 is a block diagram of the automatic blood pressure measuring instrument shown in FIG. 1.

FIG. 4 is a block diagram of the automatic blood pressure measuring instrument 100 according to an aspect of the invention shown in FIG. 1.

Of the reference numerals, 11 is for a display, 16 is for a pressure sensor, ECG LL and ECG RA are for ECG electrodes, 20 is for a pulse wave signal processing section, 30 is for an amplifying section, 40 is for a filtering section, 50 is for an ECG signal processing section, 61 is for a program storing section, 62 is for a data storing section, 63 is for an A/D converting section, 70 is for a controlling section, 80 is for an inputting section, 90 is for an interface, and 200 is for a computer.

The pulse wave signal processing section 20 amplifies and filters a pulse wave signal applied from the pressure sensor 16. The amplifying section 30 amplifies an ECG signal detected by the ECG electrodes ECG LL and ECG RA. The filtering section 40 filters an applied low band signal. The program storing section 61 stores a drive program together with set data. The data storing section 62 stores the pulse wave signal and the ECG signal together with determined data. The A/D converting section converts an analog signal into a digital signal. The controlling section determines the maximum blood pressure and the minimum blood pressure. The inputting section 80 is inputted by a manipulation signal of a user. The interface 90 is connected with an external instrument.

The pressure sensor 16 fixed to the wrist of the subject generates a pulse wave caused by a pressure of blood flowing through the artery. That is, the pressure sensor 16 fixed over the artery is subjected to impetus which the blood lends to the artery, so that the pressure sensor 16 generates the pulse wave. The pulse wave applied from the pressure sensor 16 is inputted into the pulse wave signal processing section 20, and is amplified there. As a result, the pulse wave is subjected to filtering of a low band signal and removal of a noise. Then, the signal from which the noise is removed is applied to the A/D converting section 63, and is subjected to conversion from an analog signal to a digital signal, and then is applied to the controlling section 70.

Further, the ECG electrodes ECG LL and ECG RA detect an ECG signal. The detected ECG signal is applied to and amplified by the ECG signal processing section 50, and is then applied to the A/D converting section 63. The A/D converting section 63 converts the applied analog ECG signal into a digital ECG signal to apply to the controlling section 70.

Figure 5:
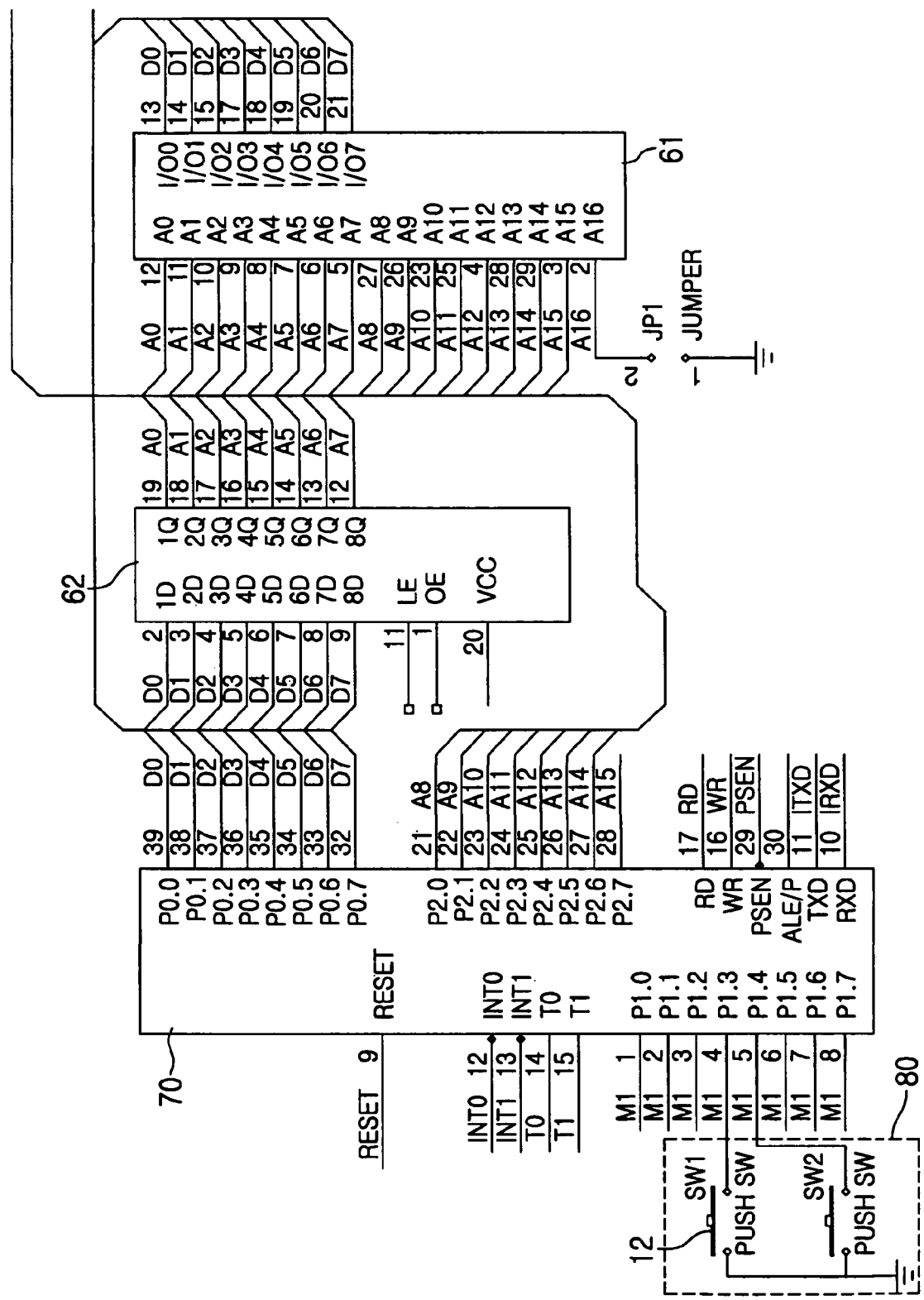
FIG. 5 is a circuit diagram of a controlling section shown in FIG. 4.

FIG. 5 is a circuit diagram of the controlling section 70 shown in FIG. 4. Here, the controlling section 70 is capable of performing arithmetical operation of data of 8 bits as shown in FIG. 5. To this end, an 8051 microprocessor having a 16-bit data address is preferably used. The controlling section 70 has four input/output ports, so that it is capable of directly receiving and outputting data of the data storing section 62 and the A/D converting section 63 relative to the outside. Further, the controlling section 70 has a built-in serial port, so that it is capable of directly receiving and outputting data from/to the computer 200 through the interface 90 using the serial port. The controlling section is capable of not only storing a program to the program storing section 61, but also performing various records related to bit operation, controlling, etc., using an SFR (special function register).

Here, it is preferred that the data storing section 62 makes use of an SRAM in order to avoid a work such as a refresh. The data storing section 62 stores data obtained by the A/D converting section 63 for a predetermined time under the control of the controlling section 70, and performs comparison and analysis of the pulse wave signal and the ECG signal based on the drive program stored in the program storing section 61. Then, the data storing section 62 determines an integral parameter a, an area parameter b, an transition time parameter c and a maximum amplitude parameter d, and then applies the determined parameters a, b, c and d to a blood pressure determination algorithm, which will be mentioned below, and finally determines values of the maximum and minimum blood pressures. The controlling section 70 stores the determined data in the data storing section 62, and controls the display 11 to display the determined values of the maximum and minimum blood pressures. Additionally, the controlling section 70 is capable of determining a pulse rate or frequency of the subject based on the applied measurement signals. A pulse rate or frequency determination algorithm for determining the pulse rate or frequency is preferably stored in the program storing section 61.

Here, the controlling section 70 checks whether there is connection to an external instrument by means of the interface 90. If the connection to an external instrument such as the computer 200, etc., is present, the controlling section 70 transmits the determined data to the computer 200 through the interface 90.

A construction of the pulse wave signal processing section 20 and the ECG signal processing section 50 as mentioned above is shown in detail in FIGS. 6 to 8. Hereinafter, the construction will be described in detail with reference to FIGS. 6 to 8.

Figure 6:
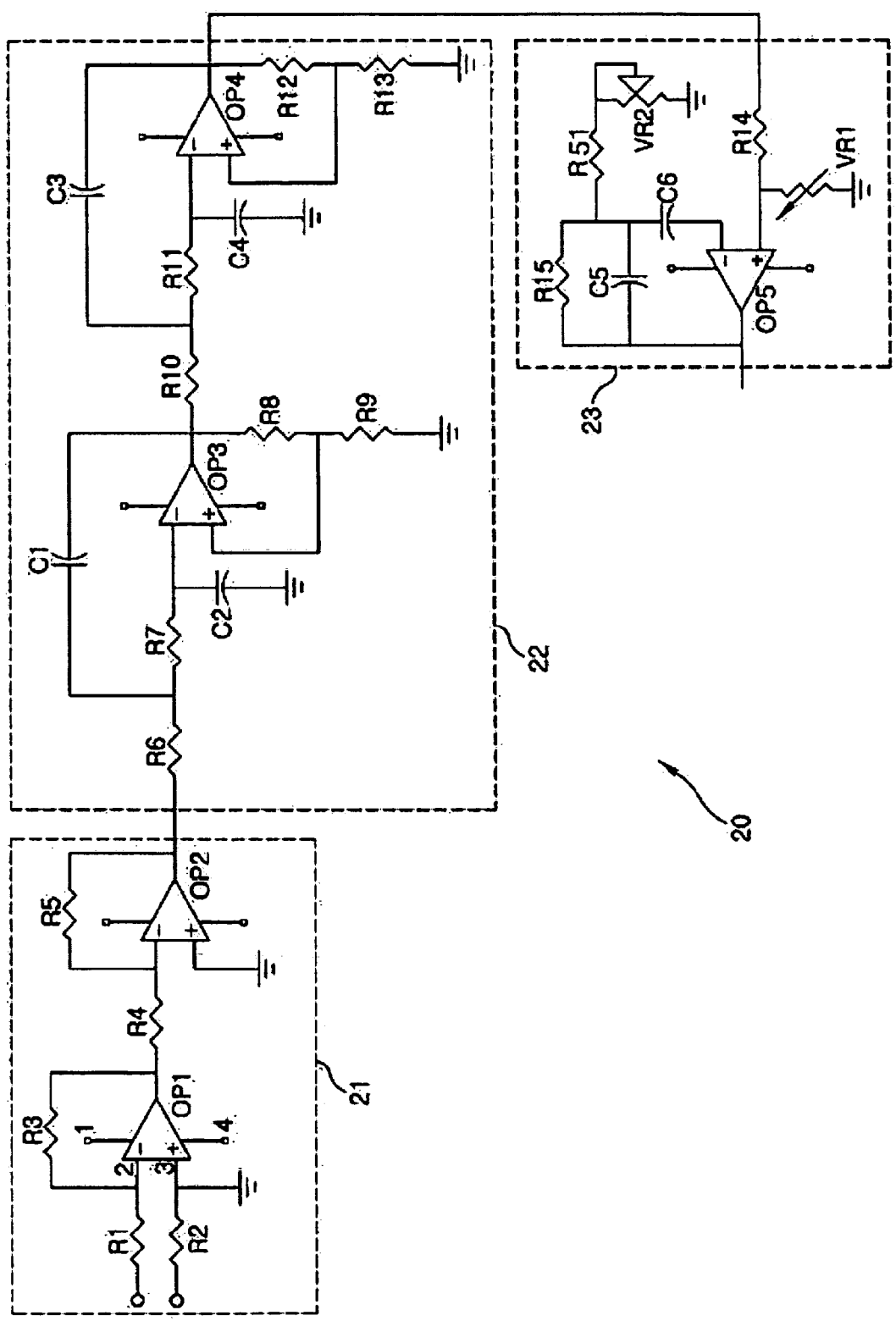
FIG. 6 is a circuit diagram of a pulse wave signal processing section shown in FIG. 4.

FIG. 6 is a circuit diagram of the pulse wave signal processing section 20 shown in FIG. 4.

Of the reference numerals, 21 indicates a first impedance matching means, 22 indicates a first low-pass filer, and 23 indicates a first notch filter.

The first impedance matching means 21 matches an impedance of the pulse wave signal applied from the pressure sensor 16 to an impedance of an output terminal. The first low-pass filter 22 filters and amplifies a low band signal to remove a noise. The first notch filter 23 removes a noise of a commercial power frequency.

When the measurement signals are applied from the pressure sensor 16, these signals are applied to inverting and non-inverting terminals of a first operational (OP) amplifier (OP1) through first and second resistors (R1 and R2) connected in parallel, and then their voltages are amplified by the first OP amplifier OP1. Here, because the applied measurement signals of the pressure sensor 16 have a higher impedance at an output terminal of the first OP amplifier OP1, both the first resistor R1 and the first OP amplifier OP1 match an impedance at each input terminal to that at each output terminal. That is, according to a rule of voltage division, when a resistance of the R1 is increased, an input voltage is lowered. The lowered input voltage is amplified at the first OP amplifier OP1, so that the impedance of the R1 is matched with that of a circuit connected to the first OP amplifier OP1. Therefore, the signals outputted from the first OP amplifier OP1 through the process as mentioned above are subjected to the foregoing impedance matching process and the amplifying process through a fourth resistor R4, and a second OP amplifier OP2.

The signals outputted from the first impedance matching means 21 pass through a sixth resistor R6, of the first low-pass filter 22, and are subjected to removal of a low band signal between 20 and 40 Hz by means of a seventh resistor R7, and a second capacitor C2, and are inputted into an inverting terminal of a third OP amplifier OP3. Then, the signals inputted into the third OP amplifier OP3 are subjected to amplification, and pass through a tenth resistor R10, and are filtered by an eleventh resistor R11 and a fourth capacitor C4. Subsequently, the filtered pulse wave signals are applied to a fourth OP amplifier OP4. The OP4 amplifies the inputted signals to apply to the first notch filter 23.

The first notch filter 23 includes a fourteenth resistor R14 connected to an output terminal of the fourth OP amplifier OP4 in series, a first variable resistor, VR1 connected to the R14 in parallel, a fifth OP amplifier OP5 having a non-inverting terminal connected to the R14 in series and an output terminal designed to perform negative feedback to an inverting terminal of the fifth OP amplifier OP5, a fifth capacitor C5 connected to a negative feedback loop of the fifth OP amplifier OP5 in series, a sixth capacitor C6 connected to the C5 in parallel and to the inverting terminal of the fifth OP amplifier OP5 in series, a fifteenth resistor R15 connected to the C5 in parallel, and a second variable resistor, VR2 having one side grounded and the other side connected to a fifty-first resistor R51, which is connected to the R15 in parallel.

The pulse wave signal applied from the first low-pass filter 22 is inputted into the first notch filter 23, particularly, the non-inverting terminal of the fifth OP amplifier OP5 via the R14 and the VR1. The pulse wave signal inputted into the fifth OP amplifier OP5 is subjected to amplification and is outputted. At this time, the R15 and the C5, which are connected in parallel on the negative feedback loop, remove a noise at a commercial power frequency of 60 Hz, which is subjected to feedback at the output terminal of the fifth OP amplifier OP5. Here, the VR1 and the VR2 are each varied to adjust the commercial power frequency to 60 Hz, so that the commercial power frequency can be matched to a commercial power frequency of a system connected with the output terminal of the first notch filter 23.

Figure 7:
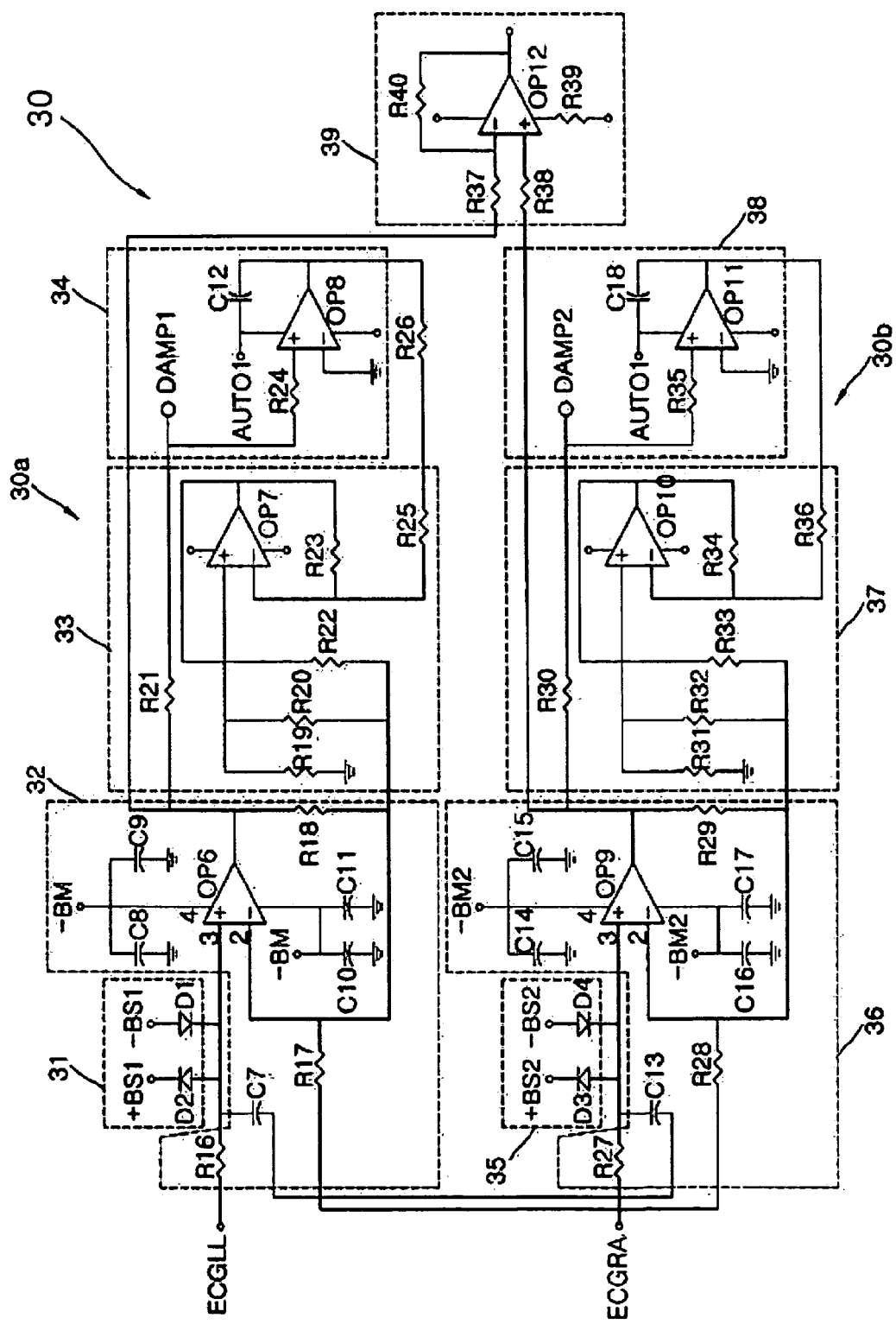
FIG. 7 is a circuit diagram of an amplifying section of an ECG signal processing section shown in FIG. 4.

FIG. 7 is a circuit diagram of the amplifying section 30 of the ECG signal processing section 50 shown in FIG. 4.

Of the reference numerals or symbols, 30a is for a first differential amplifier, 30b is for a second differential amplifier, ECG LL is for the first ECG electrode, ECG RA is for the second ECG electrode, 31 is for a first inverse current preventing means, 32 is for a first gain adjusting means, 33 is for a first ECG signal amplifying means, 34 is for a second low-pass filter, 35 is for a second inverse current preventing means, 36 is for a second gain adjusting means, 37 is for a second ECG signal amplifying means, 38 is for a third low-pass filter, and 39 is for a second impedance matching means.

The first and second inverse current preventing means 31 and 35 prevent an inverse current generated at an input power source. The first and second ECG signal amplifying means 33 and 37 amplify inputted signals. The second and third low-pass filters 34 and 38 filter signals of a low band frequency among inputted signals. The second impedance matching means 39 matches an impedance of inputted signals to that of outputted signals.

In the first differential amplifier 30a, the first gain adjusting means 32 is connected with the first ECG electrode, ECG LL in series. The inverse current preventing means 31 is connected between the ECG LL and the first gain adjusting means 32, and includes first and second power source terminals, +BS1 and −BS1 connected in parallel, and first and second diodes, D1 and D2 connected to the first and second power source terminals, +BS1 and −BS1 in an opposite direction to each other. Here, the first gain adjusting means 32 includes a sixth OP amplifier OP6. A third power source, +BM is applied to a terminal 1 of the sixth OP amplifier OP6, and a fourth power source, −BM is applied to a terminal 2 of the sixth OP amplifier OP6. The third power source, +BM is connected in parallel with eighth and ninth capacitors C8 and C9, each of which is grounded on one side. The fourth power source, −BM is connected in parallel with tenth and eleventh capacitors C10 and C11, each of which is grounded on one side. Further, the first gain adjusting means 32 is connected in parallel with the second impedance matching means 39, the first ECG signal amplifying means 33 and the second low-pass filter 34. Here, the first ECG signal amplifying means 33 includes a seventh OP amplifier OP7, an output terminal of which is subjected to negative feedback to an inverting terminal thereof. A negative feedback loop of the inverting terminal of the seventh OP amplifier OP7 is connected with an output terminal of the second low-pass filter 34. Further, the seventh OP amplifier OP7 of the first ECG signal amplifying means 33 has the output terminal connected to an output terminal of the first gain adjusting means 32.

In the second differential amplifier 30b, the second gain adjusting means 36 is connected with the second ECG electrode, ECG RA in series. The second inverse current preventing means 35 is connected between the ECG RA and the second gain adjusting means 36, and includes fifth and sixth power source terminals, +BS2 and −BS2 connected in parallel, and third and fourth diodes, D3 and D4 connected to the fifth and sixth power source terminals, +BS2 and −BS2 in an opposite direction to each other. Here, the second gain adjusting means 36 includes a ninth OP amplifier OP9. A seventh power source, −BM2 is applied to a terminal 1 of the ninth OP amplifier OP9, and an eighth power source, +BM2 is applied to a terminal 4 of the ninth OP amplifier OP9. The seventh power source, −BM2 is connected in parallel with sixteenth and seventeenth capacitors C16 and C17, each of which is grounded on one side. The eighth power source, +BM2 is connected in parallel with fourteenth and fifteenth capacitors C14 and C15, each of which is grounded on one side. Further, the second gain adjusting means 36 is connected in parallel with the second impedance matching means 39, the second ECG signal amplifying means 37 and the third low-pass filter 38. Here, the second ECG signal amplifying means 37 includes a tenth OP amplifier OP10, an output terminal of which is subjected to negative feedback to an inverting terminal thereof. A negative feedback loop of the inverting terminal of the first OP amplifier OP10 is connected with an output terminal of the third low-pass filter 38. Further, the ninth OP amplifier OP9 of the second ECG signal amplifying means 37 has the output terminal connected to an output terminal of the second gain adjusting means 36.

The first and second differential amplifiers 30a and 30b constructed as the foregoing are connected in parallel not only by seventh and thirteenth capacitors C7 and C13 at the rear ends of sixteenth and twenty-seventh resistors R16 and R27 of the input line, but also by seventeenth and twenty-eighth resistors R17 and R28 on the negative feedback loops, each of which is connected to each inverting terminal of the sixth and ninth OP amplifiers OP6 and OP9. Further, the first differential amplifier 30a is connected to an inverting terminal of the second impedance matching means 39, while the second differential amplifier 30b is connected to a non-inverting terminal of the second impedance matching means 39.

ECG signals detected by the first ECG electrode, ECG LL are applied to the first gain adjusting means 32 through the sixteenth resistor R16. Here, since ECG signals detected by the first ECG electrode, ECG LL typically have high impedances, their impedances are not matched with system-side ones, so that there is possibility to give a fatal damage to the system. Thus, input impedances are matched with the system side by the first gain adjusting means 32, and thereby a gain of output signals is adjusted to be lowered. Here, it is preferred that the R16 has a high resistance value in order to apply a rule of voltage division. Therefore, the measurement signals applied from the first ECG electrode, ECG LL are subjected to voltage division, so that a gain of the signals outputted from the sixth OP amplifier OP6 is lowered. Further, a current is applied to the first and second power source terminals, +BS1 and −BS1, so that the measurement signals have an increased current. The first and second power source terminals, +BS1 and −BS1 are respectively provided with the first and second diodes, D1 and D2, and thus the circuit is prevented from being damaged by an inverse current.

The measurement signals outputted from the first gain adjusting means 32 are inputted into a non-inverting terminal of the first ECG signal amplifying means 33 and a non-inverting terminal of the second low-pass filter 34. Here, the second low-pass filter 34 has a feedback loop from an output terminal of the eighth OP amplifier OP8 through the twelfth capacitor C12 to a terminal 1 of the eighth OP amplifier OP8. At this time, signals ranging from 20 to 40 Hz are filtered by the twelfth capacitor C12 in the feedback loop.

Therefore, the measurement signals filtered at the second low-pass filter 34 are inputted into an inverting terminal of the seventh OP amplifier OP7 of the first ECG signal amplifying means 33, and then are subjected to negative feedback from an output terminal of the seventh OP amplifier OP7 through a twenty-third resistor R23 to the inverting terminal of the seventh OP amplifier OP7, so that they are amplified and applied to the inverting terminal of the second impedance matching means 39.

An ECG signal detected by the second ECG electrode, ECG RA is applied to the second gain adjusting means 36 through the twenty-seventh resistor R27. Here, the second ECG electrode, ECG RA is considered as an external resistor as mentioned above. Since the second ECG electrode, ECG RA and the twenty-seventh resistor R27 are connected in parallel, a circuit line tapped between them is connected to a non-inverting terminal of the ninth OP amplifier OP9. Therefore, according to voltage division of the second ECG electrode, ECG RA and the twenty-seventh resistor R27, the ECG signal applied from the second ECG electrode, ECG RA is subjected to voltage division and is inputted into the ninth OP amplifier OP9, so that a gain of the signal is lowered. At this time, a current is applied to the fifth and sixth power source terminals, +BS2 and −BS2 so that the ECG signal has an increased current. The power source terminals, +BS2 and −BS2 are provided with the second inverse current preventing means 35 consisting of the third and fourth diodes, D3 and D4, and thus the circuit is prevented from being damaged by an inverse current.

The ECG signal outputted from the second gain adjusting means 36 is inputted into a non-inverting terminal of the second ECG signal amplifying means 37 and a non-inverting terminal of the third low-pass filter 38. Here, the third low-pass filter 38 has a feedback loop from an output terminal of the eleventh OP amplifier OP11 through the eighteenth capacitor C18 to a terminal 1 of the eleventh OP amplifier OP11, and thereby signals between 20 and 40 Hz are filtered.

Therefore, the measurement signals filtered at the third low-pass filter 38 are inputted into an inverting terminal of the tenth OP amplifier OP10 of the second ECG signal amplifying means 37, and then are subjected to negative feedback from an output terminal of the tenth OP amplifier OP10 through a thirty-fourth resistor R34 to the inverting terminal of the tenth OP amplifier OP10, so that they are amplified and applied to the non-inverting terminal of the second impedance matching means 39.

Thus, an output terminal of the twelfth OP amplifier OP12 of the second impedance matching means 39 is connected with a fortieth resistor R40 and forms a negative feedback loop together with an inverting terminal of the twelfth OP amplifier OP12. A voltage inputted into a thirty-seventh resistor R37 provided on an input side of the twelfth OP amplifier OP12 and a voltage inputted into the fortieth resistor R40 of the negative feedback loop are divided and inputted into the twelfth OP amplifier OP12, thus being matched with an impedance of the output terminal and applied to a filtering section 40.

Figure 8:
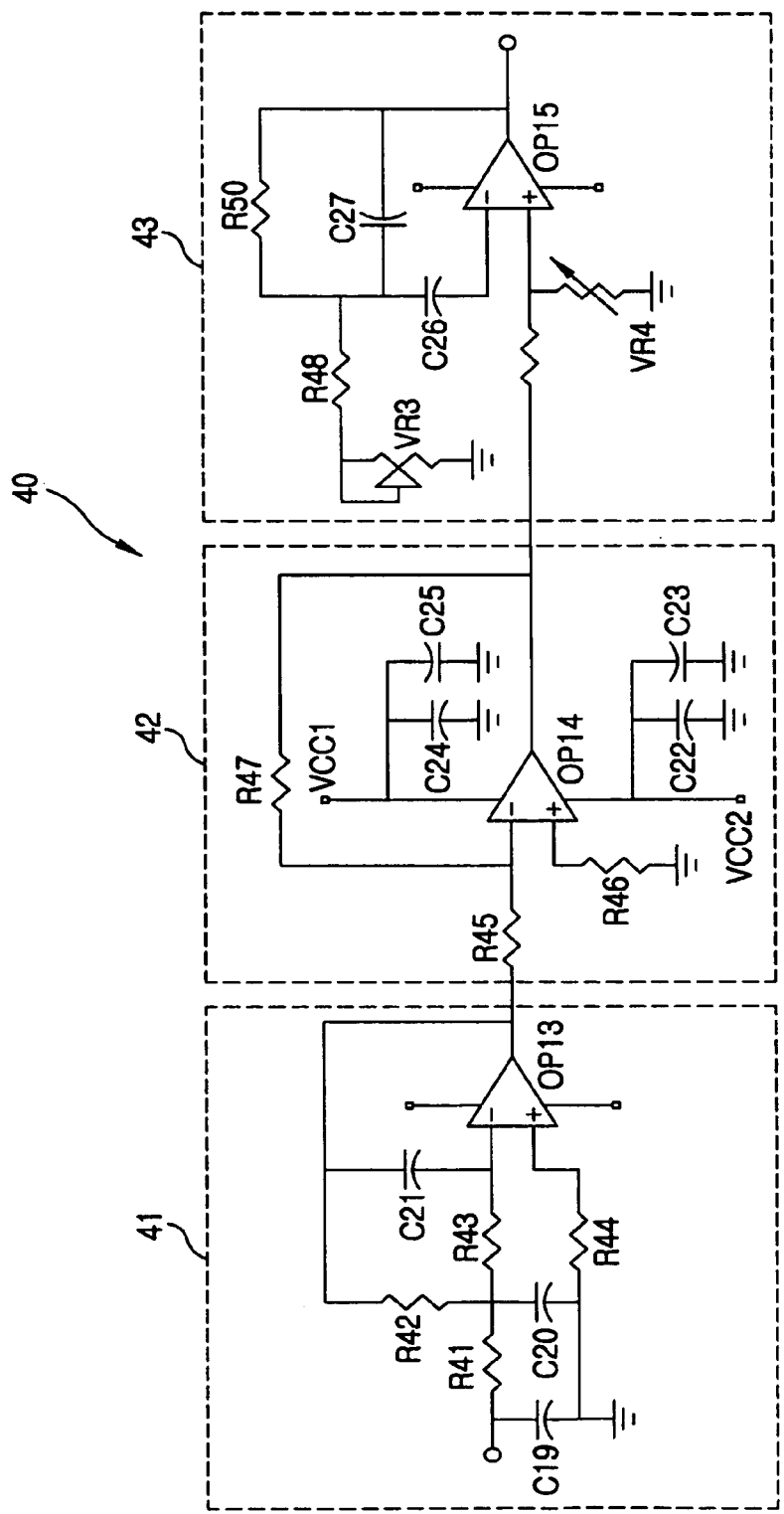
FIG. 8 is a circuit diagram of a filtering section of the ECG signal processing section shown in FIG. 4.

FIG. 8 is a circuit diagram of the filtering section 40 of the ECG signal processing section 50 shown in FIG. 4.

Of the reference numerals, 40 indicates the filtering section, 41 indicates a fourth low-pass filter, 42 indicates a third impedance matching means, and 43 indicates a second notch filter.

The fourth low-pass filter 41 removes a noise of low band from applied signals. The third impedance matching means 42 matches an impedance of an input terminal with that of an output terminal. The second notch filter 43 removes a noise of a commercial power frequency.

In the fourth low-pass filter 41, an input terminal is connected in parallel with a nineteenth capacitor C19, and is connected in series with a forty-first resistor R41, a forty-third resistor R43 and an inverting terminal of a thirteenth OP amplifier OP13. A twentieth capacitor C20 is connected in parallel between the forty-first resistor R41, the forty-third resistor R43. A forty-fourth resistor R44 is connected to the nineteenth and twentieth capacitors C19 and C20 on one side and to a non-inverting terminal of the thirteenth OP amplifier OP13 on the other side. Here, the thirteenth OP amplifier OP13 has a negative feedback loop from an output terminal to the non-inverting terminal. Here, a forty-second resistor R42 and a twenty-first capacitor C21 are each connected in parallel to the negative feedback loop.

The third impedance matching means 42 has a forty-fifth resistor 45 R45 connected in series with the output terminal of the fourth low-pass filter 41. The forty-fifth resistor 45 R45 is connected in series to an inverting terminal of a fourteenth OP amplifier OP14. A forty-sixth resistor R46 is connected to a non-inverting terminal of the fourteenth OP amplifier OP14 on one side, and is grounded on the other side. The fourteenth OP amplifier OP14 has a terminal 1 to which a commercial power source, VCC1 is applied. The commercial power source, VCC1 is connected in parallel with twenty-fourth and twenty-fifth capacitors C24 and C25. The fourteenth OP amplifier OP14 has a terminal 4 to which another commercial power source, VCC2 is applied. The commercial power source, VCC2 is connected in parallel with twenty-second and twenty-third capacitors C22 and C23. Thus, a noise is removed from the applied power source. The fourteenth OP amplifier OP14 has a negative feedback loop from an output terminal to an inverting terminal. A forty-seventh resistor 47 is connected to the negative feedback loop of the fourteenth OP amplifier OP14.

The second notch filter 43 has a forty-ninth resistor R49, one side of which is connected in series with the third impedance matching means 42 and the other side is connected in series with a non-inverting terminal of a fifteenth OP amplifier OP15. Here, a fourth variable resistor, VR4 is connected in parallel between the forty-ninth resistor R49 and the non-inverting terminal of the fifteenth OP amplifier OP15. Further, the fifteenth OP amplifier OP15 is formed with a feedback loop from an output terminal to an inverting terminal. A fiftieth resistor R50 and a twenty-seventh capacitor C27 are each connected in parallel to the feedback loop of the fifteenth OP amplifier OP15. A third variable resistor, VR3 is connected in parallel with the fiftieth resistor R50 through a forty-eighth resistor R48. A twenty-sixth capacitor C26 is connected in parallel with the fiftieth resistor R50 and the twenty-seventh capacitor C27 on one side, and with the inverting terminal of the fifteenth OP amplifier OP15 on the other side.

From the measurement signals applied at the amplifying section 30, low band signals between 20 and 40 Hz are filtered by the forty-first and forty-third resistors R41 and R43, and by the nineteenth and twentieth capacitors C19 and C20. The filtered signals are applied to and amplified by the thirteenth OP amplifier OP13. Here, the amplified signals are applied to the negative feedback loop of the output terminal again, and are filtered by the forty-second resistor R42 and the twenty-first capacitor C21, and are applied to the inverting terminal of the thirteenth OP amplifier OP13.

As mentioned above, the signals filtered at the fourth low-pass filter 41 are inputted into the inverting terminal of the fourteenth OP amplifier OP14 through the forty-fifth resistor R45 of the third impedance matching means 42, so that a voltage amplified to the output terminal is inputted into the inverting terminal again along the negative feedback loop. Therefore, according to a rule of voltage division, the inputted signals are subjected to voltage division at the forty-fifth and forty-seventh resistors R45 and R47. The voltage-divided signals are amplified again and outputted, thus being matched with an impedance of the second notch filter 43.

The signals outputted from the third impedance matching means 42 are applied to the non-inverting terminal of the fifteenth OP amplifier OP15 through the forty-ninth resistor R49 of the second notch filter 43. Here, the fourth variable resistor VR4 adjusts a commercial power frequency of the inputted signals. That is, the commercial power frequency is ideally 60 Hz, but is from 58 to 59 Hz in reality, so that it is adjusted and matched at the fourth variable resistor VR4. The signals amplified at the fifteenth OP amplifier OP15 are subjected to negative feedback, and are filtered at the fiftieth resistor R50 and the twenty-seventh capacitor C27, and are subjected to removal of a noise of the commercial power frequency. At this time, the signals are adjusted to the commercial power frequency by adjustment of the third and fourth variable resistors VR3 and VR4.

Figure 9:
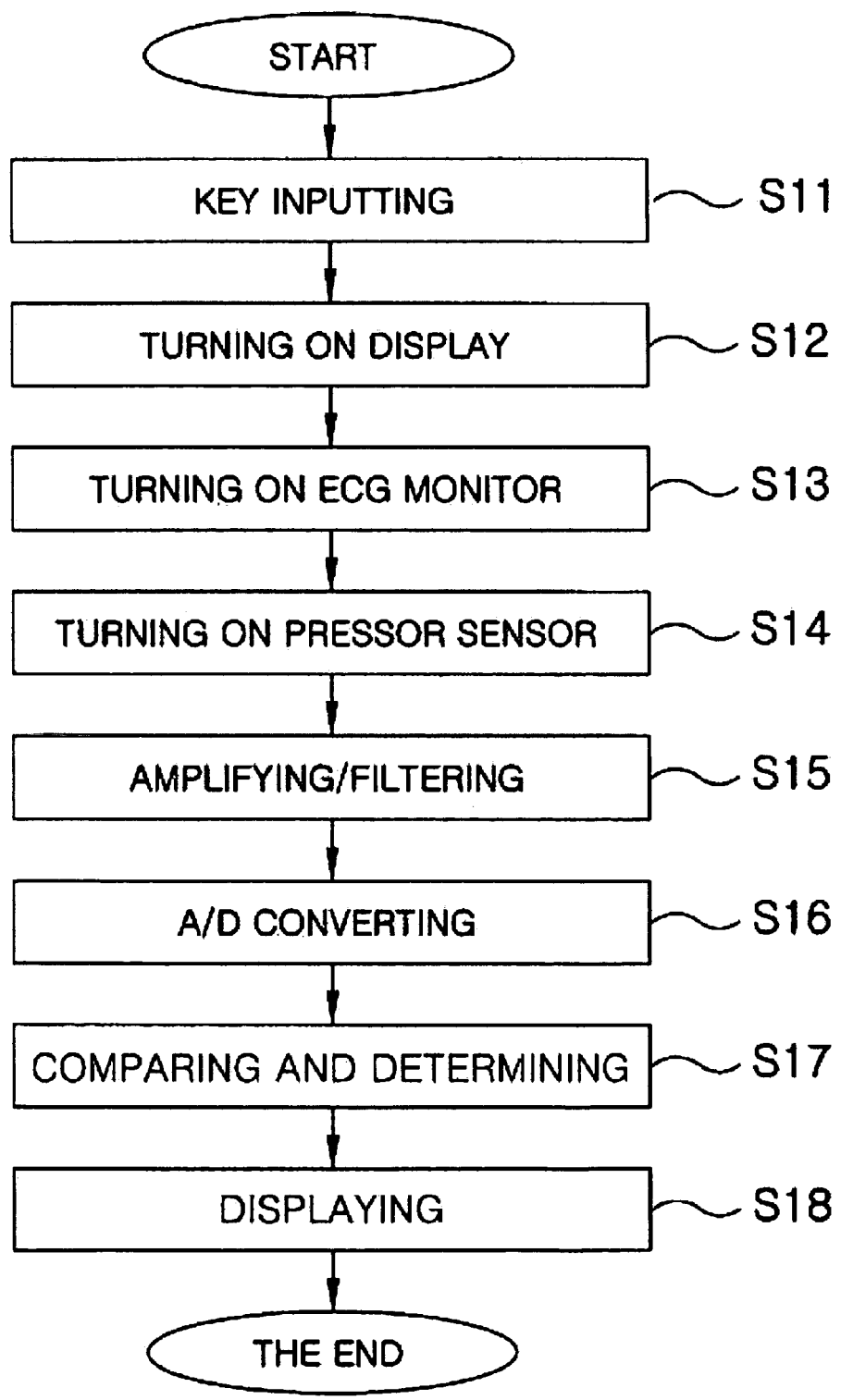
FIG. 9 is a flow chart of an automatic blood pressure measuring method according to an aspect of the invention.

FIG. 9 is a flow chart of an automatic blood pressure measuring method according to an aspect of the invention. An operation of the example of the invention described above will be described in detail with reference to FIG. 9.

The automatic blood pressure measuring instrument 100 according to an aspect of the is fixed to the right wrist of the subject so as to position the pressure sensor 16 over the artery of the subject. The first ECG electrode ECG LL and the second ECG electrode ECG RA are connected to the ECG connection ports 13 provided on one side of the automatic blood pressure measuring instrument 100. The first ECG electrode ECG LL is fixed to the left leg of the subject, while the second ECG electrode ECG RA is fixed to the right arm of the subject.

A power switch provided on the upper surface of the automatic blood pressure measuring instrument is turned on (block S11), the display 11 is operated (block S12), and the pressure sensor 16, the first ECG electrode ECG LL, and the second ECG electrode ECG RA generate sensing signals (blocks S13 and S14). Therefore, the pulse wave signal sensed at the pressure sensor 16 is applied to the pulse wave signal processing section 20, so that the pulse wave signal outputted from the pressure sensor 16 has an impedance matched with that of the signals outputted from the first impedance matching means 21, and are amplified by the first low-pass filter 22, and are applied to the first notch filter 23 again, and are subjected to noise removal at the commercial power frequency of 60 Hz (block S15). Then, the analog signals free from a noise are converted into digital signals by the A/D converting section 63 and then applied to the controlling section 70 (block S16).

Further, the ECG signal detected by the first ECG electrode ECG LL and the second ECG electrode ECG RA is applied to and amplified at the amplifying section 30. That is, the ECG signal detected at the left leg by the first ECG electrode ECG LL is amplified at the first differential amplifier 30a, and is applied to the inverting terminal of the second impedance matching means 39, while the ECG signal detected at the right arm by the second ECG electrode ECG RA is amplified at the second differential amplifier 30b, and are applied to the non-inverting terminal of the second impedance matching means 39, so that both signals are matched with an impedance of the filtering section 40 and are applied to the filtering section 40.

Thus, the amplified signals are applied to the filtering section 40, the fourth low-pass filter 41 allows for pass only some of the amplified signals belonging to a predetermined band, but removes the rest. The filtered ECG measurement signals are applied to the third impedance matching means 42. The third impedance matching means 42 performs buffering in order to match the inputted signals to the second notch filter 43 on the output side of the filtering section 40. The buffered signals are applied to the second notch filter 43, and subjected to noise removal of the commercial power frequency of 60 Hz, and applied to the A/D converting section 63, so that they are subjected to conversion from the analog signals to digital signals and applied to the controlling section (blocks S15 and S16).

The controlling section 70 stores the applied measurement signals in the data storing section 62 for a predetermined time, reads them out, compares them and determines the integral parameter a, the area parameter b, the transition time parameter c, and the maximum amplitude parameter d. The controlling section 70 uses a blood pressure determination algorithm stored in the program storing section 61 that is a function of these parameters to determine the maximum and minimum blood pressures, and displays these blood pressures on the display 11 (blocks S17 and S18).

Further, the controlling section 70 determines pulse rate and diagnosis result using the measurement signals stored in the data storing section 62 for a predetermined time. That is, the controlling section 70 controls to apply the measurement signals to a pulse rate and diagnosis result algorithm for the pulse rate and diagnosis result stored in the data storing section 62, to determine the pulse rate and diagnosis result to display them on the display 11.

Here, the blood pressure, the pulse rate and the diagnosis result are displayed on the LCD (Liquid Crystal Display) 11, so that limitation to a displayed quantity is removed. The display 11 is adapted to display the maximum and minimum blood pressure measured by the automatic blood pressure measuring instrument 100, as well as the pulse rate and the present diagnosis result. Further, the display 11 is designed to display cardiovascular disease codes, an output mode of which is developed based on expected cardiovascular diseases. Table 1 shows items displayed on the display 11 including the disease codes as one example.

TABLE 1

Example of Expected Disease Codes

| Symptom | Code | Symptom | Code |
| --- | --- | --- | --- |
| Normal | Nomal | Unstable high blood pressure | H-Case S |
| High normal blood pressure | H-Case 0 | First period of high blood pressure | H-Case 1 |
| Low blood pressure | L-Case | Second period of high blood pressure | H-Case 2 |
| Slow pulse | B-Case | Third period of high blood pressure | H-Case 3 |
| Weak pulse | T-Case | Fourth period of high blood pressure | H-Case 4 |
| Weak beat of artrim | A-Case | Re-measuring request | ERROR |

Figure 10:
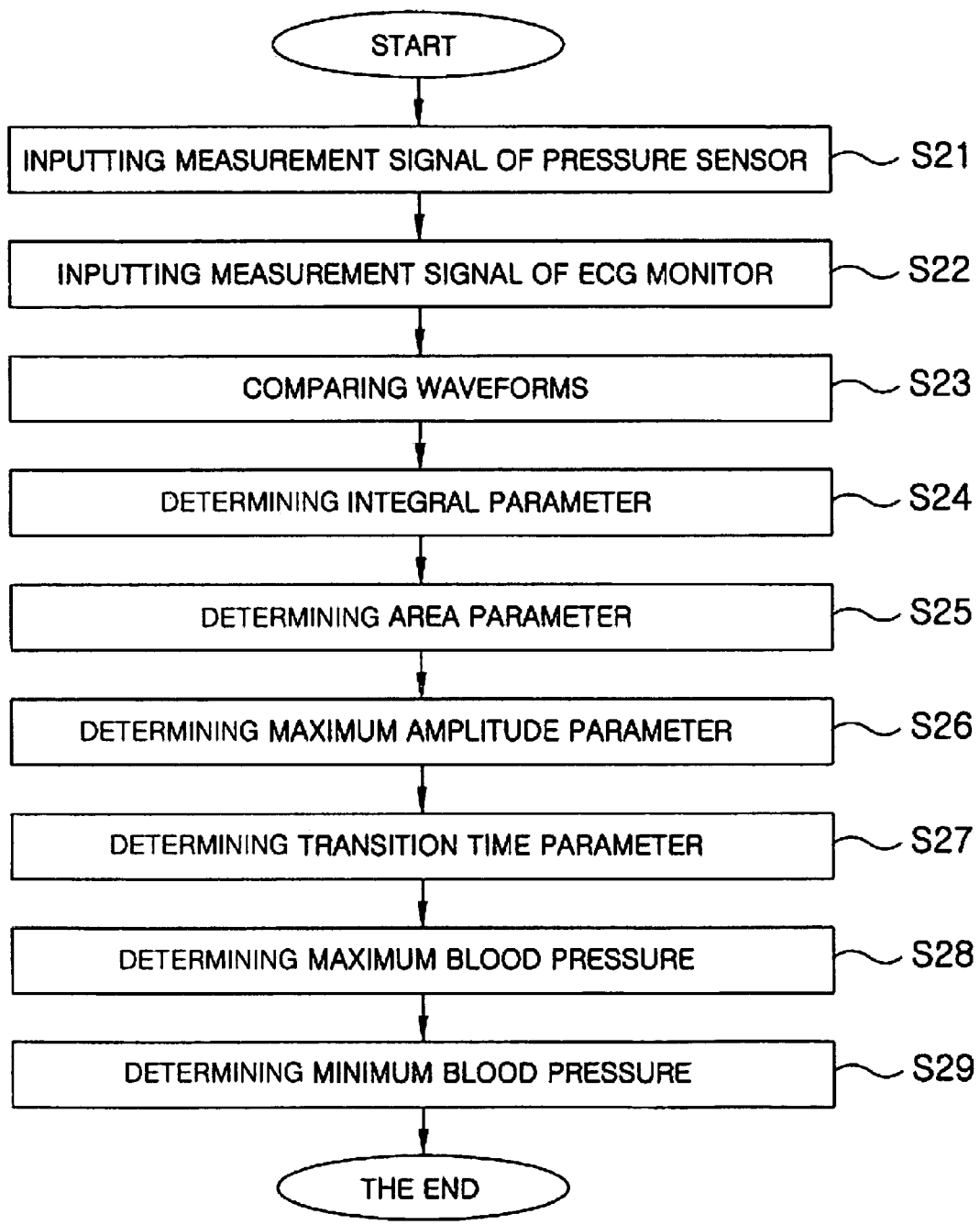
FIG. 10 is a flow chart of a comparing and determining block shown in FIG. 9.
Figure 11:
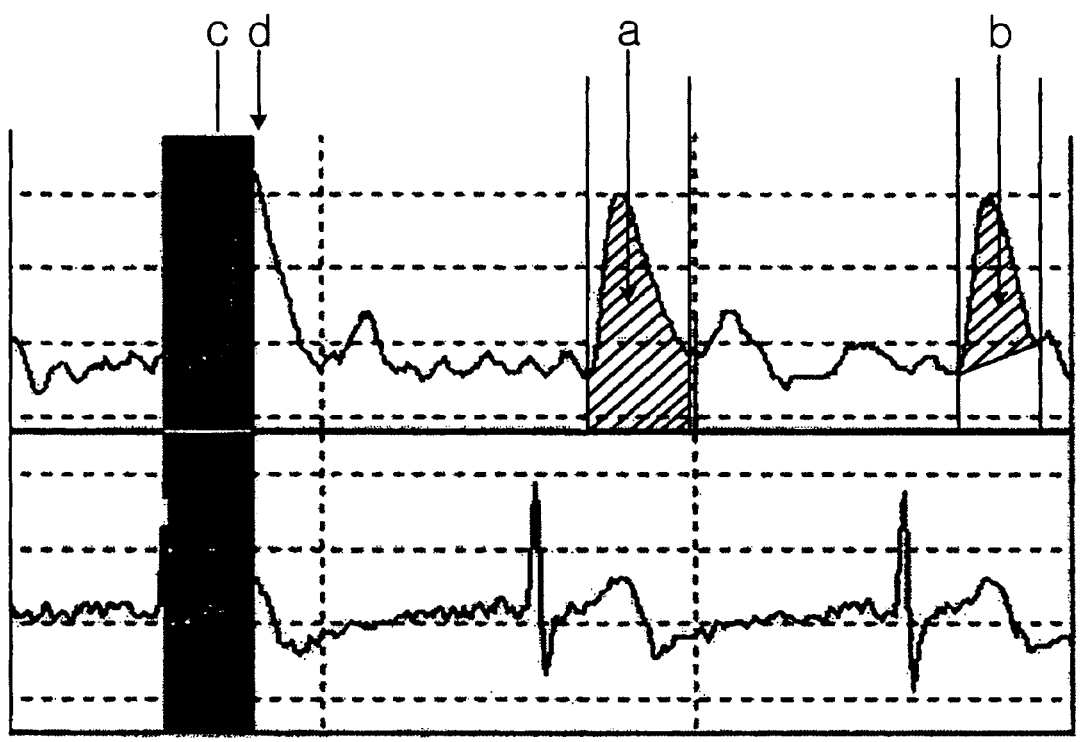
FIG. 11 is a graph of a pulse wave signal and an ECG signal showing parameters that are determined in FIG. 10.

FIG. 10 is a flow chart of the comparing and determining block S17 shown in FIG. 9. FIG. 11 is a graph of a pulse wave signal and an ECG signal showing parameters that are determined in FIG. 10. The comparing and block S17 will be described in detail with reference to FIGS. 10 and 11.

When the pulse wave signal and the ECG signal generated from the pressure sensor 16 and the ECG electrodes ECG LL and ECG RA are temporarily stored in the data storing section 62 through the A/D converting section 63 (blocks S21 and S22), the controlling section 70 reads out the measurement signals stored in the data storing section 62 after a predetermined time lapses away, compares waveforms of the two signals (block S23) and determines each parameter. That is, as shown in FIG. 11, the pulse wave signal and the ECG signal are compared and analyzed, and each parameter is determined. Of the reference symbols, a is the integral parameter, b is the area parameter, c is the transition time parameter, and d is the maximum amplitude parameter.

Thus, the controlling section 70 reads out the data stored temporarily in the data storing section 62, selects a zone, and determines the integral parameter a according to the following equation with an integral value for data values between end points of the selected zone (block S24).

$$f_{output}(n) = \sum_{k=1}^{n} [(f_{input}(k-1) + f_{input}(k))/2] * \Delta T$$

Here, f( ) is a data value, n is a number of sampling intervals each having a width $\Delta t$ on the horizontal axis in FIG. 11, k=0 is the left end point of the selected zone and k=n is the right end point of the selected zone.

Further, the controlling section 70 sets a base line joining end points of the area selected within the predetermined zone, and integrates a zone of the upper side of the base line to obtain the area parameter b (block S25). This calculation value will be always a positive value, and can be measured as the whole area between the waveform and the base line, and can represent the area in terms of a unit obtained by multiplying a unit of the amplitude by a unit of the horizontal axis, and can be calculated using the following equation.

$$f_{output}(n) = \sum_{k=1}^{n} [(|f_{input}(k-1) - y(k-1)| + |(f_{input}(k) - y(k)|)/2] * \Delta T$$

Here, f( ) is a data value, y( ) is a value of the line joining the end points, n is a number of sampling intervals each having a width Δt on the horizontal axis in FIG. 11, k=0 is the left end point of the selected zone and k=n is the right end point of the selected zone.

The controlling section 70 determines a time interval between the maximum amplitudes of an ECG waveform and a waveform detected from the pressure sensor fixed to the wrist, and determines the transition time parameter c (block S26), and determines the maximum amplitude within a designated range of the integral and area parameters a and b, thus determining the maximum amplitude parameter d (block S27). The maximum amplitude parameter d derives a change of the maximum amplitude value of the detected waveform according to a pressure change.

Here, the parameters a, b, c and d determined in the foregoing way represent constant tendencies of the systolic and diastolic blood pressures. This linear change is shown in FIGS. 12A through 12D and FIGS. 13A and 13B.

Figure 12A:
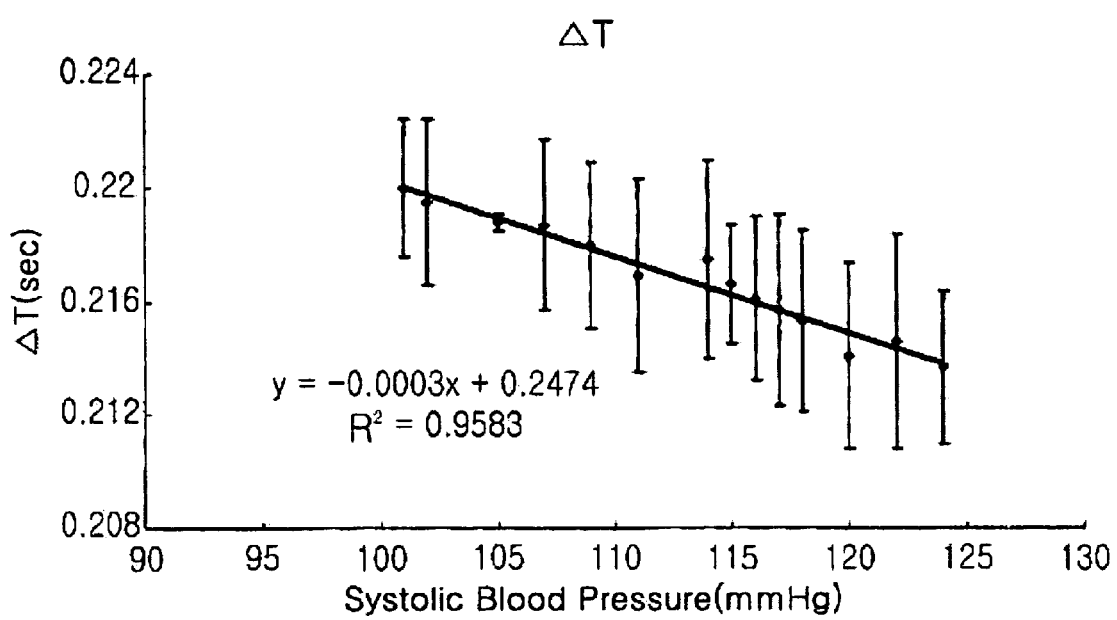
FIGS. 12A though 12D are graphs showing changes in the parameters shown in FIG. 11 according to a change in a systolic blood pressure.

FIG. 12A is a graph showing a change in the transition time parameter c (ΔT) according to a change in the systolic blood pressure. It can be seen that as the systolic blood pressure becomes higher, a time interval between maximum amplitudes decreases. Thus, a value of the transition time parameter c also decreases.

Figure 12B:
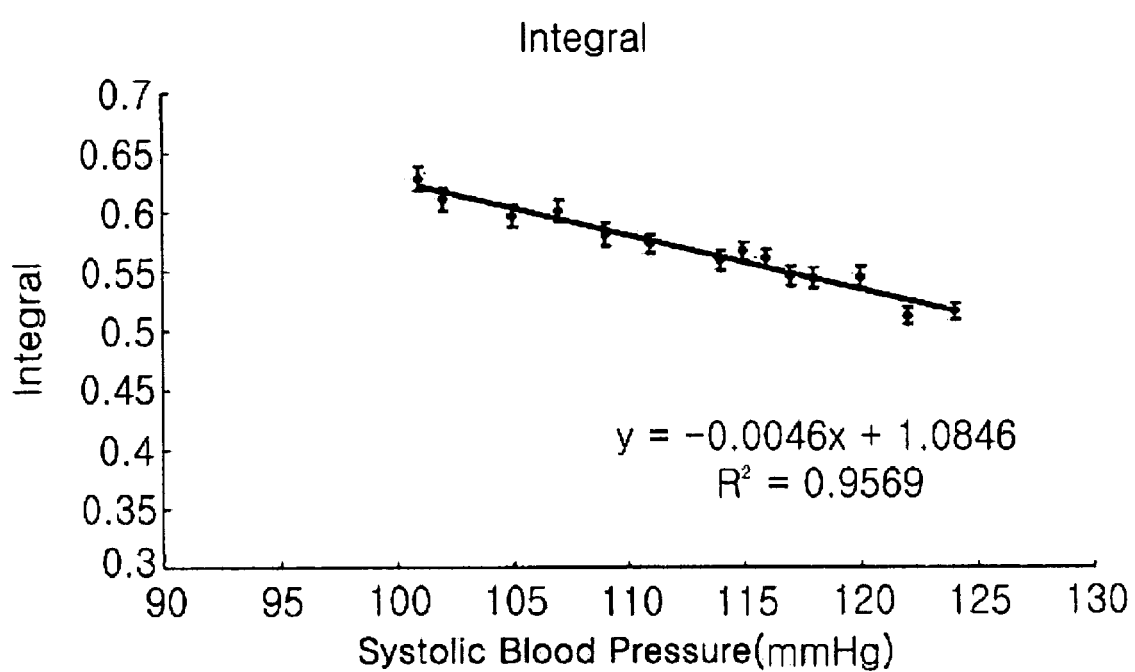

FIG. 12B is a graph showing a change in the integral parameter a according to a change in the systolic blood pressure. It can be seen that as the systolic blood pressure becomes higher, an integral value decreases within a predetermined range. Thus, a value of the integral parameter a also decreases.

Figure 12C:
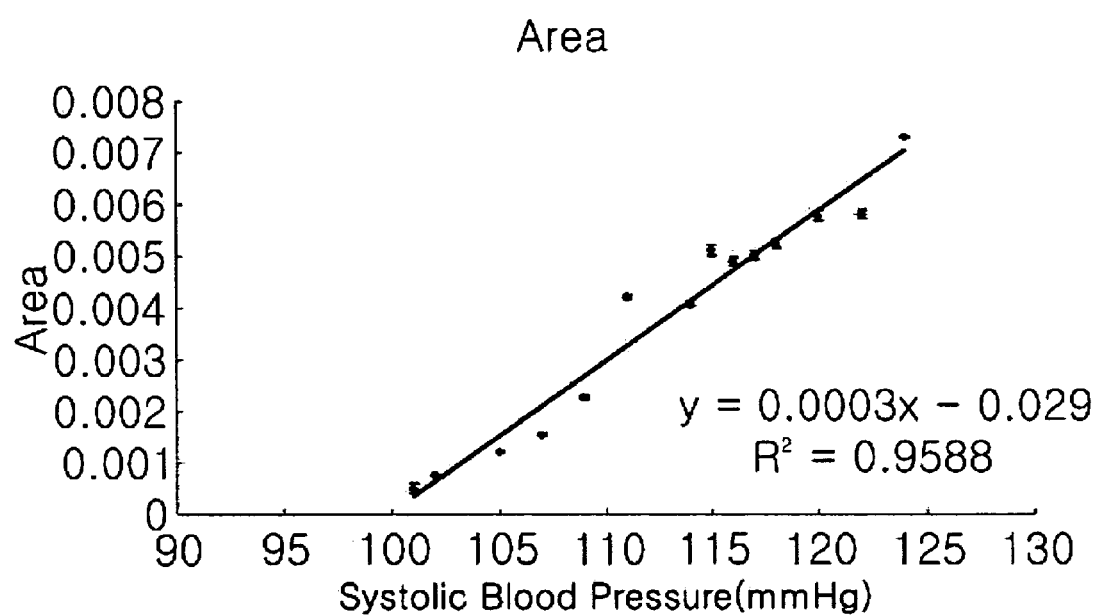

FIG. 12C is a graph showing a change in the area parameter b according to a change in the systolic blood pressure. As the systolic blood pressure becomes higher, a value of data increases within a predetermined area. Thus, a value of the area parameter b also increases.

Figure 12D:
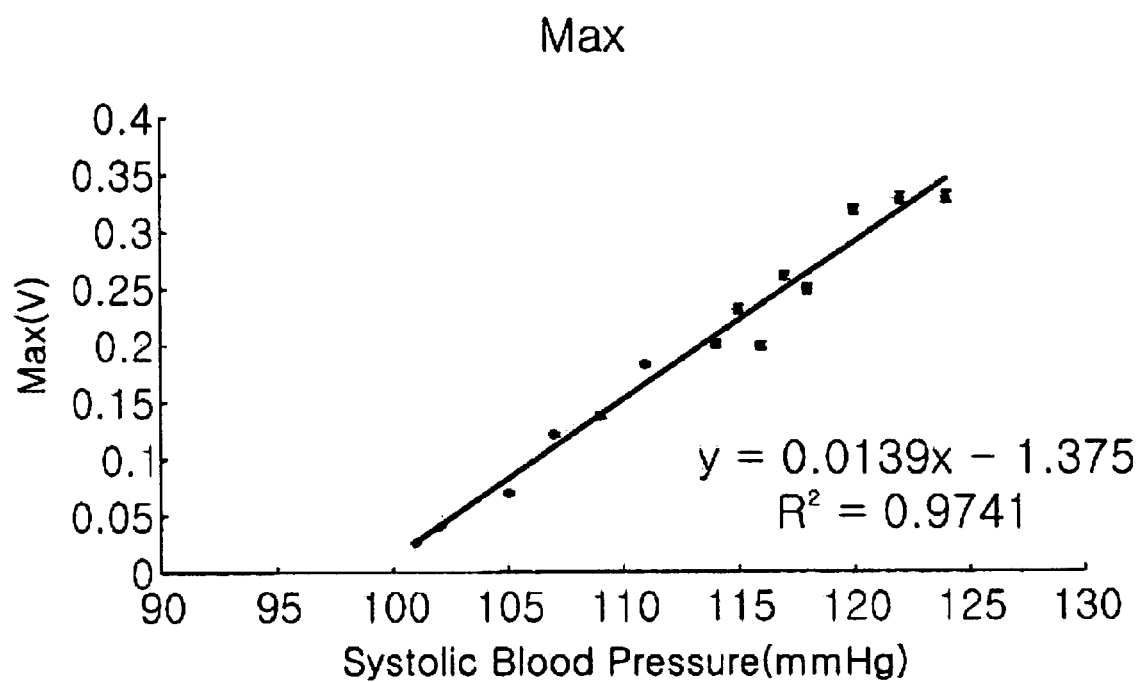

FIG. 12D is a graph showing a change in the maximum amplitude parameter d (Max) according to a change in the systolic blood pressure. As the systolic blood pressure becomes higher, a value of the maximum amplitude parameter d also increases.

Figure 13A:
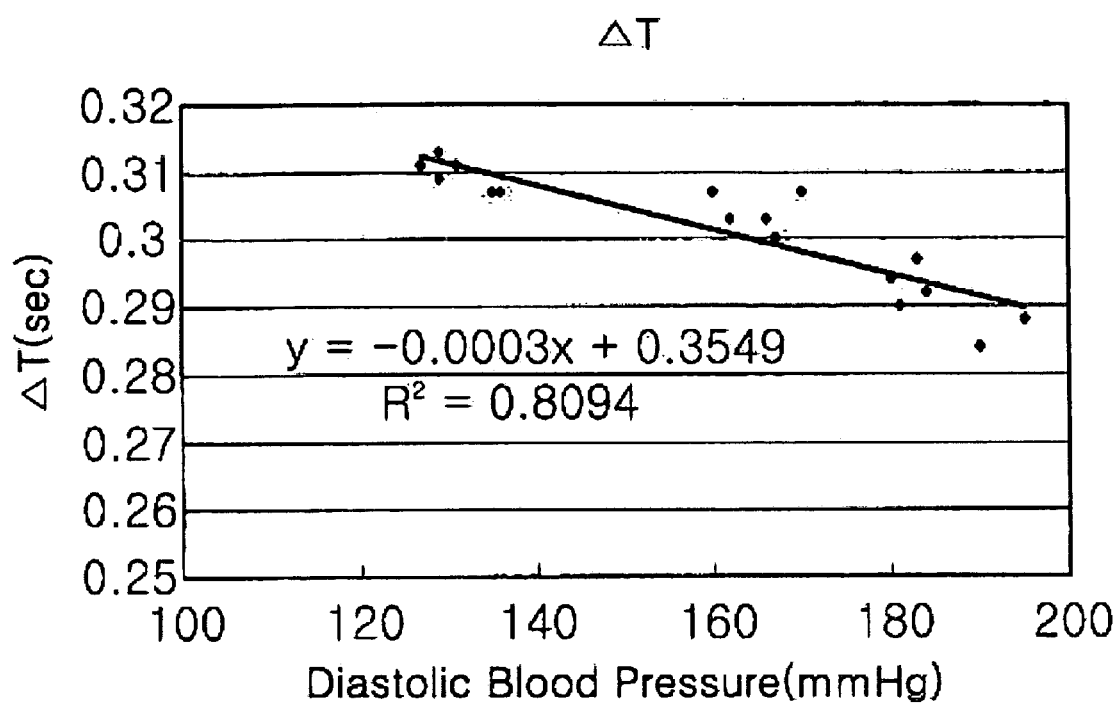
FIGS. 13A and 13B are graphs showing changes in two of the parameters shown in FIG. 11 according to a change in a diastolic blood pressure.

FIG. 13A is a graph showing a change in the transition time parameter c (ΔT) according to a change in the diastolic blood pressure. As the diastolic blood pressure becomes higher, a value of the transition time parameter c linearly decreases.

Figure 13B:
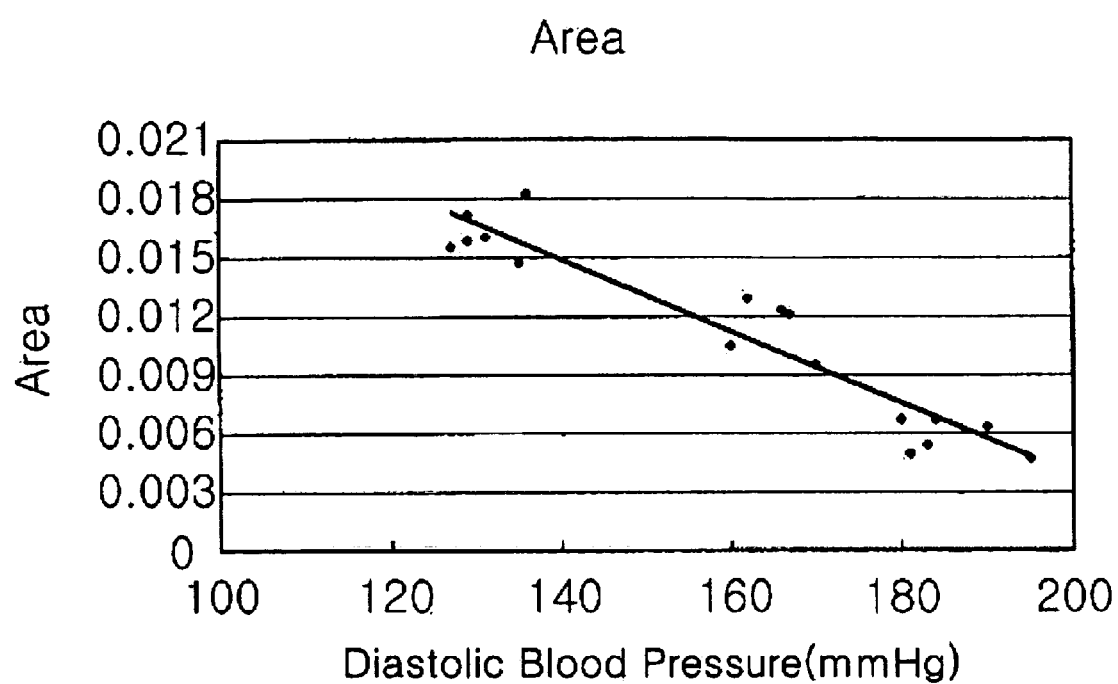

FIG. 13B is a graph showing a change in the area parameter b according to a change in the diastolic blood pressure. As the diastolic blood pressure becomes higher, a value of the area parameter b decreases.

As for the correlation of each parameter shown in FIGS. 12A through 12D, as the systolic blood pressure increases, the integral parameter a and the transition time parameter c linearly decrease, and the area parameter b and the maximum amplitude parameter d linearly decrease.

As for the correlation of each parameter shown in FIGS. 13A and 13B, as the diastolic blood pressure increases, the transition time parameter c and the area parameter b linearly decrease.

Using the correlation between the systolic and diastolic blood pressures and the parameters a, b, c and d, an aspect of the invention uses a blood pressure determination algorithm as follows:

Maximum blood pressure (systolic blood pressure)

$P = 919.121 \cdot Ar + 17.157 \cdot Max - 98.26 \cdot Int + 161.736 \cdot \Delta T$ Minimum blood pressure (diastolic blood pressure)

$P = 146.161 - 78.903 \cdot \Delta T - 442.904 \cdot Ar$ where P is pressure in mm Hg, Int is the integral parameter a, Ar is the area parameter b, ΔT is the transition time parameter c in seconds, and Max is the maximum amplitude parameter d.

The maximum blood pressure refers to the systolic blood pressure. The formula for the maximum blood pressure is derived using the correlation between the four parameters and the systolic blood pressure. The minimum blood pressure refers to the diastolic blood pressure. The formula for the minimum blood pressure is derived using the correlation between the diastolic blood pressure and the transition time parameter c and the area parameter b.

Further, in the blood pressure determination algorithm, a series of constants by which the parameters a, b, c and d are multiplied refer to quantities by which the parameters a, b, c and d are varied according to the blood pressure, and represent a specific weight of each parameter according to the change of the blood pressure. That is, the constant is for statistically representing a change rate of the blood pressure as the parameters a, b, c and d are changed.

Therefore, the controlling section 70 applies the parameters a, b, c and d determined in the foregoing process to the blood pressure determination algorithm to determine the maximum (systolic) blood pressure (block S28) and the minimum (diastolic) blood pressure (block S29), and displays the determined maximum and minimum blood pressures on the display 11 (block S18 in FIG. 9).

Figure 14:
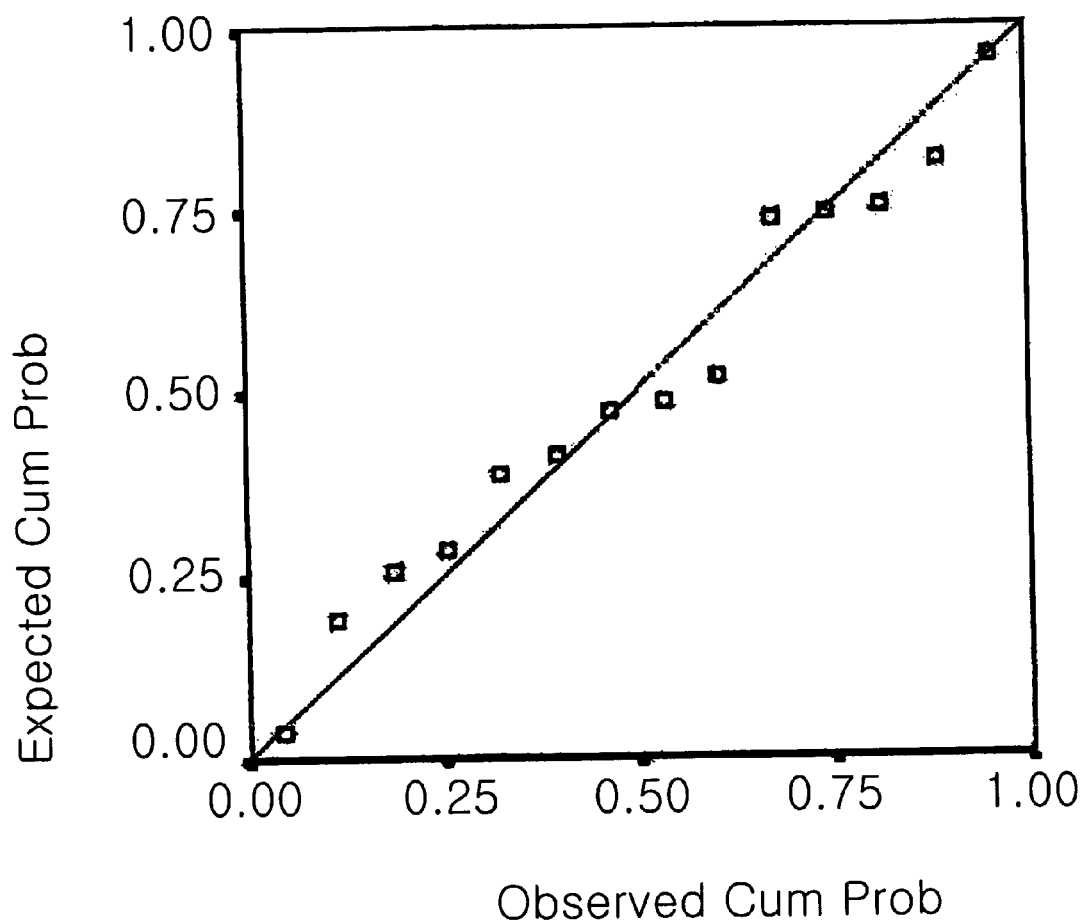
FIG. 14 is a graph of a cumulative distribution of expected values versus a cumulative distribution of observed values for a blood pressure determination algorithm using the parameters shown in FIG. 11.

FIG. 14 is a graph of a cumulative distribution of expected values versus a cumulative distribution of observed values for a blood pressure determination algorithm using the parameters described above and shown in FIG. 11.

As shown, the graph is a straight line when the expected values are the same as the observed values. By observing how standardized residuals are distributed relative to an expected straight line, the two distributions can be compared. The result is that, because the standardized residuals are near a normal distribution, the blood pressure measurement using the automatic blood pressure measuring instrument and method according to an aspect of the invention has a very high degree of prediction.

The automatic blood pressure measuring instrument according to an aspect of the invention using a pressure sensor such as a piezo sensor measures a blood pressure using correlation between a pulse wave signal and an ECG signal, and can be used to measure blood pressures of all persons, including infants, low blood pressure patients, and intensive care patients, because it makes use of various parameters determined by comparing and analyzing the pulse wave signal and the ECG signal, such as a transition time parameter, an integral parameter, an area parameter and a maximum amplitude parameter.

Additionally, it is possible to measure a blood pressure without inserting a catheter into an artery. Thus, it is possible to prevent various disadvantages which have attracted attention in an existing invasive blood measuring method, such as a circulatory problem, infection, a blood clot and so on, and to measure an accurate blood pressure with more ease and safety. Further, it is possible to change a concept on an existing uncomfortable and inaccurate blood pressure measurement. It is expected that a future-oriented and high-tech and multifunctional blood pressure measuring instrument will be distributed at an exponential speed, and that request for industrialization will be rapidly increased, and that due to the advent of brand-new multifunctional microwave hemadynamometer, technical application to a domestic medical instrument field will be much expanded.

Although several embodiments of the invention have been shown and described, it would be appreciated by those skilled in the art that changes may be made in these embodiments without departing from the principles and spirit of the invention, the scope of which is defined in the claims and their equivalents.

What is claimed is:

1. An automatic blood pressure measuring instrument for measuring and displaying a blood pressure of a subject in a non-invasive manner, comprising:
   a pressure sensor for obtaining a pulse wave signal from a wrist of the subject;
   a pulse wave signal processing section for amplifying, filtering, and removing noise from the pulse wave signal obtained by the pressure sensor to obtain a processed analog pulse wave signal;
   electrocardiogram electrodes for detecting an electrocardiogram signal of the subject;
   an electrocardiogram signal processing section for amplifying, filtering, and removing noise from the electrocardiogram signal detected by the electrocardiogram electrodes to obtain a processed analog electrocardiogram signal;
   an A/D converting section for converting the processed analog pulse wave signal and the processed analog electrocardiogram signal into a digital pulse wave signal and a digital electrocardiogram signal;
   a controlling section for comparing and analyzing the digital pulse wave signal and the digital electrocardiogram signal to determine parameters comprising a transition time parameter, an integral parameter, an area parameter, and a maximum amplitude parameter, and determining the blood pressure of the subject based on the transition time parameter, the integral parameter, the area parameter, and the maximum amplitude parameter; and
   a display for displaying the blood pressure of the subject determined by the controlling section.

2. The automatic blood pressure measuring instrument of claim 1, further comprising:
   a program storing section for storing an operation program of the controlling section; and
   a data storing section for storing the digital pulse wave signal and the digital electrocardiogram signal for a predetermined time, and storing data determined by the controlling section.

3. The automatic blood pressure measuring instrument of claim 1, wherein the pulse wave signal processing section comprises:
   a first impedance matching means for matching an impedance of the pulse wave signal to an output signal of the first impedance matching means;
   a first low-pass filter for filtering and amplifying the output signal of the first impedance matching means to produce a filtered and amplified output signal; and
   a first notch filter for removing noise having a commercial power frequency from the filtered and amplified output signal of the first low-Pass filter to produce the processed analog pulse wave signal.

4. The automatic blood pressure measuring instrument of claim 3, wherein the first notch filter comprises:
   an operational amplifier for amplifying the filtered and amplified output signal of the first low-pass filter to produce the processed analog pulse wave signal, the operational amplifier comprising an inverting terminal, a non-inverting terminal, and an output terminal, the filtered and amplified output signal of the first low-pass filter being coupled to the non-inverting terminal of the operational amplifier, the processed analog pulse wave signal being produced at the output terminal of the operational amplifier;
   a negative feedback loop connected between the output terminal of the operational amplifier and the inverting terminal, the negative feedback loop comprising a filter for removing the noise having the commercial power frequency;
   a first variable resistor connected between the non-inverting terminal of the operational amplifier and a ground; and
   a second variable resistor coupled between the filter of the negative feedback loop and the ground;
   wherein the first variable resistor and the second variable resistor adjust a frequency of the noise removed by the filter of the negative feedback loop.

5. The automatic blood pressure measuring instrument of claim 1, wherein the electrocardiogram signal processing section comprises:
   an amplifying section for amplifying the electrocardiogram signal detected by the electrocardiogram electrodes to produce an amplified output signal; and
   a filtering section for filtering and removing noise from the amplified output signal of the amplifying section to produce the processed analog electrocardiogram signal.

6. The automatic blood pressure measuring instrument of claim 5, wherein the filtering section comprises:
   a fourth low-pass filter for removing noise from the amplified output signal of the amplifying section;
   a third impedance matching means for matching an impedance of the output signal of the fourth low-pass filter to an impedance of an output signal of the third impedance matching means; and
   a second notch filter for removing noise having a commercial power frequency from the output signal of the third impedance matching means to produce the processed analog electrocardiogram signal.

7. The automatic blood pressure measuring instrument of claim 5, wherein the electrocardiogram electrodes comprise:
   a first electrocardiogram electrode for detecting the electrocardiogram signal at a location on a first side of a body of the subject; and
   a second electrocardiogram electrode for detecting the electrocardiogram signal at a location on a second side of the body of the subject opposite to the first side of the body of the subject;

wherein the amplifying section comprises:
a first differential amplifier comprising:
a first gain adjusting means for adjusting a gain of the electrocardiogram signal detected by the first electrocardiogram electrode to produce a gain-adjusted output signal;
a second low-pass filter for removing a low band noise from the gain-adjusted output signal of the first gain adjusting means to produce a filtered output signal; and
a first electrocardiogram signal amplifying means for amplifying the filtered output signal of the second low-pass filter to produce a first amplified electrocardiogram signal;
a second differential amplifier comprising:
a second gain adjusting means for adjusting a gain of the electrocardiogram signal detected by the second electrocardiogram electrode to produce a gain-adjusted output signal;
a third low-pass filter for removing a low band noise from the gain-adjusted output signal of the second gain adjusting means to produce a filtered output signal; and
a second electrocardiogram signal amplifying means for amplifying the filtered output signal of the third low-pass filter to produce a second amplified electrocardiogram signal; and
a second impedance matching means for combining the first amplified electrocardiogram signal with the second amplified electrocardiogram signal to produce the amplified output signal of the amplifying section so that the amplified output signal of the amplifying section has an impedance matching an impedance of the filtering section.

8. The automatic blood pressure measuring instrument of claim 7, wherein the first gain adjusting mean comprises a first input terminal having the first electrocardiogram electrode connected thereto;
wherein the second gain adjusting means comprises a second input terminal having the second electrocardiogram electrode connected thereto;
wherein the first differential amplifier further comprises a first inverse current preventing means coupled to the first input terminal of the first gain adjusting means; and
wherein the second differential amplifier further comprises a second inverse current preventing means coupled to the second input terminal of the second gain adjusting means.

9. An automatic blood pressure measuring method for measuring and displaying a blood pressure of a subject in a non-invasive manner, comprising:
obtaining a pulse wave signal from a wrist of the subject;
amplifying, filtering, and removing noise from the pulse wave signal to obtain a processed analog pulse wave signal;
detecting an electrocardiogram signal of the subject;
amplifying, filtering, and removing noise from the electrocardiogram signal to obtain a processed analog electrocardiogram signal;
converting the processed analog pulse wave signal and the processed analog electrocardiogram signal into a digital pulse wave signal and a digital electrocardiogram signal;
comparing and analyzing the digital pulse wave signal and the digital electrocardiogram signal to determine parameters comprising a transition time parameter, an integral parameter, an area parameter, and a maximum amplitude parameter;
determining the blood pressure of the subject based on the transition time parameter, the integral parameter, the area parameter, and the maximum amplitude parameter; and
displaying the determined blood pressure of the subject.

10. The automatic blood pressure measuring method of claim 9, wherein the determining of the blood pressure of the subject comprises:
determining a systolic blood pressure of the subject based on the transition time parameter, the integral parameter, the area parameter, and the maximum amplitude parameter; and
determining a diastolic blood pressure of the subject based on the transition time parameter and the area parameter but not the integral parameter or the maximum amplitude parameter; and
wherein the displaying of the determined blood pressure of the subject comprises:
displaying the determined systolic blood pressure of the subject; and
displaying the determined diastolic blood pressure of the subject.

11. The automatic blood pressure measuring method of claim 9, wherein the transition time parameter is a time interval between a maximum amplitude of a waveform of the digital pulse wave signal and a maximum amplitude of a waveform of the digital electrocardiogram signal.

12. The automatic blood pressure measuring method of claim 9, wherein the integral parameter is an integral value of a data value of the digital pulse wave signal between end points of a selected zone of the digital pulse wave signal.

13. The automatic blood pressure measuring method of claim 9, wherein the area parameter is an integral value of a difference between a data value of the digital pulse wave signal between end points of a selected zone of the digital pulse wave signal and a value of a base line joining points where a waveform of the digital pulse wave signal intersects the end points of the selected zone of the digital pulse wave signal.

14. The automatic blood pressure measuring method of claim 9, wherein the maximum amplitude parameter is a maximum amplitude of a waveform of the digital pulse wave signal within a selected zone of the digital pulse wave signal.

15. The automatic blood pressure measuring instrument of claim 1, wherein the controlling section determines a systolic blood pressure of the subject based on the transition time parameter, the integral parameter, the area parameter, and the maximum amplitude parameter;
wherein the controlling section determines a diastolic blood pressure of the subject based on the transition time parameter and the area parameter but not the integral parameter or the maximum amplitude parameter; and
wherein the display displays the systolic blood pressure of the subject determined by the controlling section, and displays the diastolic blood pressure of the subject determined by the controlling section.

16. The automatic blood pressure measuring instrument of claim 15, wherein the controlling section determines the systolic blood pressure of the subject using the following systolic blood pressure determination algorithm:

$$P = 919.121 \cdot Ar + 17.157 \cdot Max - 98.26 \cdot Int + 161.736 \, \Delta T$$

where Ar is the area parameter, Max is the maximum amplitude parameter, Int is the integral parameter, and $\Delta T$ is the transition time parameter; and wherein the controlling section determines the diastolic blood pressure of the subject using the following diastolic blood pressure determination algorithm:

$$P=146.161-78.903 \cdot \Delta T - 442.904 \cdot Ar$$

where $\Delta T$ is the transition time parameter and Ar is the area parameter.

17. The automatic blood pressure measuring method of claim 10, wherein the determining of the systolic blood pressure of the subject comprises determining the systolic blood pressure of the subject using the following systolic blood pressure determination algorithm:

$$P=919.121 \cdot Ar + 17.157 \cdot Max - 98.26 \cdot Int + 161.736 \cdot \Delta T$$

where Ar is the area parameter, Max is the maximum amplitude parameter, Int is the integral parameter, and $\Delta T$ is the transition time parameter; and wherein the determining of the diastolic blood pressure of the subject comprises determining the diastolic blood pressure of the subject using the following diastolic blood pressure determination algorithm:

$$P=146.161-78.903 \cdot \Delta T - 442.904 \cdot Ar$$

where $\Delta T$ is the transition time parameter and Ar is the area parameter.

* * * * *